US011285006B2

(12) United States Patent
Mujwid et al.

(10) Patent No.: US 11,285,006 B2
(45) Date of Patent: Mar. 29, 2022

(54) INFLATABLE PENILE PROSTHESIS WITH VALVES FOR INCREASING FLOW EFFICIENCY

(71) Applicant: Boston Scientific Scimed, Inc., Maple Grove, MN (US)

(72) Inventors: James Ryan Mujwid, Hudson, WI (US); Ryan Earl Fredrick, Eden Prairie, MN (US); John Anders Bostrom, Saint Paul, MN (US); Thomas Andrew Albrecht, Edina, MN (US); Jessica Elizabeth Felton, Minneapolis, MN (US); Gary A. Rocheleau, Plymouth, MN (US); Travis J. Schauer, Delano, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 199 days.

(21) Appl. No.: 16/377,480

(22) Filed: Apr. 8, 2019

(65) Prior Publication Data
US 2019/0307567 A1  Oct. 10, 2019

Related U.S. Application Data

(60) Provisional application No. 62/654,837, filed on Apr. 9, 2018.

(51) Int. Cl.
*A61F 2/26* (2006.01)
(52) U.S. Cl.
CPC ........ *A61F 2/26* (2013.01); *A61F 2250/0013* (2013.01); *A61F 2250/0069* (2013.01)

(58) Field of Classification Search
CPC ....................................................... A61F 2/26
See application file for complete search history.

(56) References Cited

U.S. PATENT DOCUMENTS

| 4,699,128 A | 10/1987 | Hemmeter et al. |
| 4,895,139 A | 1/1990 | Hauschild et al. |
| 5,010,882 A | 4/1991 | Polyak et al. |
| 5,141,509 A | 8/1992 | Burton et al. |
| 6,240,962 B1 | 6/2001 | Tai et al. |
| 6,334,761 B1 | 1/2002 | Tai et al. |

(Continued)

OTHER PUBLICATIONS

International Search Report and Written Opinion for Application No. PCT/US2019/026452, dated Jul. 25, 2019, 15 pages.

*Primary Examiner* — John P Lacyk
(74) *Attorney, Agent, or Firm* — Brake Hughes Bellermann LLP

(57) ABSTRACT

According to an aspect, an inflatable penile prosthesis includes a reservoir configured to hold fluid, an inflatable member, and a pump assembly configured to facilitate a transfer of a fluid from the reservoir to the inflatable member. The pump assembly includes a pump bulb, and a valve body defining a fluid passageway. The valve body includes a refill valve disposed in the fluid passageway. The refill valve includes a valve member. In response to the pump bulb being compressed, the valve member moves within the fluid passageway in a first direction to a closed position in which the valve member blocks the fluid from being transferred around the refill valve. In response to the pump bulb being uncompressed, the valve member moves within the fluid passageway in a second direction to an open position in which the valve member allows the fluid to transfer around the refill valve.

19 Claims, 25 Drawing Sheets

(56) References Cited

U.S. PATENT DOCUMENTS

| | | |
|---|---|---|
| 8,568,294 B2 | 10/2013 | Ellering |
| 8,617,052 B2 | 12/2013 | Fogarty |
| 8,632,456 B2 | 1/2014 | Fogarty et al. |
| 8,932,203 B2 | 1/2015 | Ellering |
| 8,932,204 B2 | 1/2015 | Fogarty et al. |
| 8,939,889 B1 | 1/2015 | Chechik |
| 8,974,370 B2 | 3/2015 | Chechik |
| 9,186,251 B2 | 11/2015 | Fogarty et al. |
| 2002/0082471 A1 | 6/2002 | Henkel et al. |
| 2007/0142700 A1 | 6/2007 | Fogarty et al. |
| 2010/0056859 A1 | 3/2010 | Kuyava et al. |
| 2013/0072751 A1 | 3/2013 | Fogarty |
| 2013/0303841 A1 | 11/2013 | Fogarty |
| 2018/0071101 A1 | 3/2018 | Daniel |
| 2019/0307567 A1 | 10/2019 | Mujwid et al. | ns with valves for increasing flow
INFLATABLE PENILE PROSTHESIS WITH VALVES FOR INCREASING FLOW EFFICIENCY

CROSS-REFERENCE TO RELATED APPLICATION

This application is a Nonprovisional of, and claims priority to, U.S. Patent Application No. 62/654,837, filed on Apr. 9, 2018, entitled "INFLATABLE PENILE PROSTHESIS WITH VALVES FOR INCREASING FLOW EFFICIENCY", which is incorporated by reference herein in its entirety.

TECHNICAL FIELD

This disclosure relates generally to bodily implants and more specifically to bodily implants, such as penile prosthesis that includes a refill valve and/or an inflation valve.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. In some existing devices, the pump mechanism includes a pump bulb that creates a vacuum by expanding after a manual compression, which is applied by a patient or physician. This expansion creates negative pressure (vacuum) pulling fluid through a refill valve (from the fluid reservoir to the pump bulb). Then, compression of the pump bulb results in pressure rising in the pump bulb until the point at which an inflation valve opens which allows the fluid to transfer out of the pump valve and into the inflatable cylinders. Multiple compression cycles eventually leads to the inflatable members reaching a limit in volume which then results in increased cylinder pressure. Increased cylinder pressure results in higher valve crack pressures which also results in reduced fluid volume transfer.

In some existing devices, the flow efficiency of the refill valve and the flow efficiency of the inflation valve may be limited by the vacuum created from the re-expansion of the pump bulb, the springs required to return the valves to a sealed position, as well as other sub-optimal channel artifacts (e.g., fluid path corners, oversized cavities, kink resistance tubing (KRT) restriction, heavy return spring, adhesive backfill, reservoir collapse, etc.). As such, conventional refill and inflation valves may contain fluid flow restrictions that decrease the flow efficiency.

SUMMARY

According to an aspect, an inflatable penile prosthesis includes a reservoir configured to hold fluid, an inflatable member, and a pump assembly configured to facilitate a transfer of a fluid from the reservoir to the inflatable member. The pump assembly includes a pump bulb, and a valve body defining a fluid passageway. The valve body includes a refill valve disposed in the fluid passageway. The refill valve includes a valve member. In response to the pump bulb being compressed, the valve member moves within the fluid passageway in a first direction to a closed position in which the valve member blocks the fluid from being transferred around the refill valve. In response to the pump bulb being uncompressed, the valve member moves within the fluid passageway in a second direction to an open position in which the valve member allows the fluid to transfer around the refill valve.

According to an aspect, the inflatable penile prosthesis may include one or more of the following features (or any combination thereof). The valve member may include a valve seat portion configured to block the fluid passageway in response to the valve member being in the closed position. The valve member may include a tapered seat portion configured to block the fluid passageway in response to the valve member being in the closed position. The valve member may define a plurality of grooves. The refill valve may include a first guide member that extends from a first side of the valve member in the first direction, and a second guide member that extends from a second side of the valve member in the second direction. The first guide member may include a plurality of grooves. The valve body may include a plurality of protrusions that extend into the fluid passageway, the plurality of protrusions being configured to contact the valve member in response to the valve member being in the open position. The refill valve may be devoid of a biasing member that biases the valve member to either the closed position or open position. The fluid passageway may be a first fluid passageway, and the valve body may include a second fluid passageway and an inflation valve disposed within the second fluid passageway. The inflation valve may include a valve member disposed within the second fluid passageway and configured to move between an open position and a closed position. The inflation valve may include a biasing member configured to bias the valve member of the inflation valve to the closed position. The valve member of the inflation valve may include a valve seat portion configured to block the second fluid passageway in response to the valve member of the inflation valve being in the closed position. The inflation valve may include a first guide member that extends from the valve member of the inflation valve in the first direction, and a second guide member that extends from the valve member of the inflation valve in the second direction.

According to an aspect, a valve assembly for an inflatable penile prosthesis includes a valve body having a first fluid passageway for transfer of fluid between a reservoir and a pump bulb and a second fluid passageway for transfer of fluid between the pump bulb and an inflatable member, and a refill valve disposed in the first fluid passageway. The refill valve has a valve member. In response to the pump bulb being compressed, the valve member moves within the first fluid passageway in a first direction to a closed position in which the valve member blocks the fluid from being transferred around the refill valve. In response to the pump bulb being uncompressed, the valve member moves within the first fluid passageway in a second direction to an open position in which the valve member allows the fluid to transfer around the refill valve. The valve assembly includes an inflation valve disposed in the second fluid passageway.

According to an aspect, the valve assembly may include one or more of the following features (or any combination thereof). The inflation valve may include a valve member and a biasing member disposed within the second fluid passageway. The biasing member may bias the valve member of the inflation valve to a closed position. The second fluid passageway may include a first flow section having a first size, a second flow section having a second size, and a central section disposed between the first flow section and the second flow section. The central section has a third size, and the valve member of the inflation valve and the biasing member may be disposed within the central section. The third size may be larger than the second size. The inflation valve may include a flapper valve. The flapper valve may include an outer structural member, a cut pattern, and a valve head. The valve head may be configured to move away from the outer structural member in response to fluid force. The first fluid passageway may include a first cylindrical section having a first diameter, a second cylindrical section having a second diameter, a central cylindrical section disposed between the first cylindrical section and the second cylindrical section. The central cylindrical section has a third diameter. The valve member of the refill valve may be disposed within the central cylindrical section. The third diameter may be larger than the second diameter.

According to an aspect, an inflatable penile prosthesis includes a reservoir configured to hold fluid, an inflatable member, and a pump assembly configured to facilitate a transfer of a fluid from the reservoir to the inflatable member. The pump assembly includes a pump bulb, and a valve body defining a first fluid passageway and a second fluid passageway. The valve body includes a refill valve disposed in the first fluid passageway, and an inflation valve disposed in the second fluid passageway. At least one of the refill valve and the inflation valve includes a flapper valve.

According to an aspect, the inflatable penile prosthesis may include one or more of the following features (or any combination thereof). The flapper valve may include an outer structural member, at least one spring strut, and a valve head. The outer structural member, the at least one spring strut, and the valve head may substantially lie in a same plane in response to the flapper valve being within a closed position. The valve head may be disposed in a different plane than the outer structural member in response to the flapper valve being within an open position. The flapper valve may include a valve head layer, an elastomeric seal layer, and a backplate layer. The elastomeric seal layer may be disposed between the valve head layer and the backplate layer.

DETAILED DESCRIPTION

Figure 1:
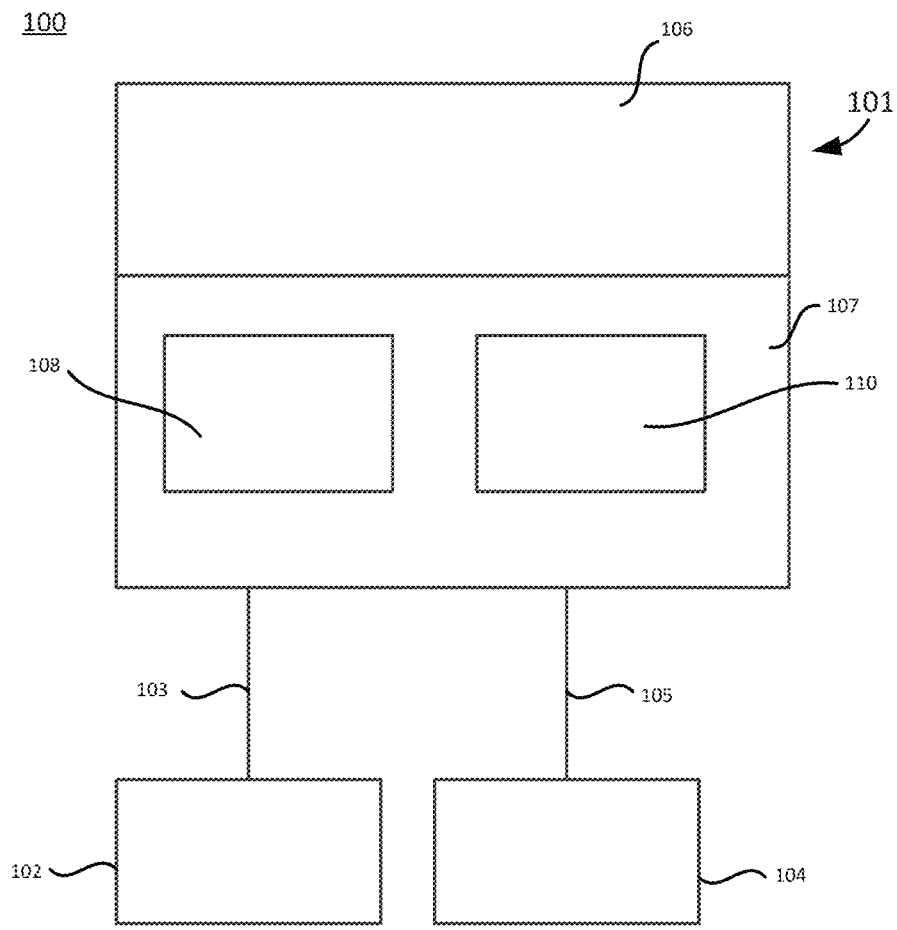
FIG. 1 schematically illustrates a penile prosthesis according to an aspect.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The embodiments discussed herein provide a refill valve assembly within an inflatable penile prosthesis that can improve the refill valve's flow efficiency. For example, the design of the refill valve assembly may reduce (or remove) one or more of the following sub-optimal flow restrictions: fluid path corners, oversized cavities, KRT restrictions, and reservoir collapse. As a result, the flow efficiency is increased and the amount of time required for inflating the inflatable members is reduced (e.g., reduced refill time), which improves device performance and patient satisfaction. Also, the refill valve assembly discussed herein may reduce the chance of patient misuse where they attempt to re-squeeze the pump bulb before it is refilled. Also, the refill valve assembly discussed herein provides a more simplified design that can improve the device's reliability and consistency of operation due to the lack of springs, as well as the removal of some operator assembly steps carried out by the patient or physician (e.g., the steps of spring positioning and/or poppet alignment can be removed).

The embodiments discussed herein provide an inflation valve assembly within an inflatable penile prosthesis that can improve the inflation valve's flow efficiency. For example, the design of the inflation valve may reduce (or remove) one or more of the following sub-optimal flow restrictions: fluid path corners, oversized cavities, KRT restrictions, heavy return spring on inflation poppet, and adhesive backfill. As a result, the inflation valve assembly discussed herein may reduce the overall effort to operate the system. For example, the time required for filling the inflation members may be decreased, and the force required to compress the pump bulb may be decreased. Stated another way, the inflation valve discussed herein provides a reduced fill time and reduced effort to achieve a specific flow rate via reduced flow restrictions. Also, the inflation valve discussed herein may improve device reliability and consistency of operation due to the alignment of the valve within the channel, single functionality, and simplified operator assembly steps (e.g., spring positioning, poppet stack alignment, bonding).

FIG. 1 schematically illustrates an inflatable penile prosthesis 100 according to an aspect. The inflatable penile prosthesis 100 may include a reservoir 102, an inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 includes a pump bulb 106 and a valve body 107. In some examples, the pump bulb 106 may include a flexible member defining a cavity. In some examples, the pump bulb 106 may define a pump shell having a flexible bulb and a valve body connector, where the valve body connector is designed to fit at least partially over the valve body 107. In some examples, the pump bulb 106 may include a squeeze pump. In some examples, the pump bulb 106 may include a portion that is round or substantially round. In some examples, the pump bulb 106 may include ribbing or dimples to aid the user in gripping the pump bulb 106. The pump bulb 106 may use suction and pressure to move the fluid in and out of the cavity of the pump bulb 106 in the inflation mode. For example, the user may depress or squeeze the pump bulb 106 to expel the fluid out of the cavity, and, when the flexible member returns to its original shape, the resulting suction pushes the fluid into the cavity of the pump bulb 106. In some examples, the pump bulb 106 may have a bulb spring rate that is designed to refill the pump bulb 106 in a selected time frame.

The pump bulb 106 may be squeezed or depressed by the user in order to facilitate the transfer of fluid from the reservoir 102 to the inflatable member 104. For example, in the inflation mode, while the user is operating the pump bulb 106, the pump bulb 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump bulb 106 to the reservoir 102.

The valve body 107 includes a refill valve 108 and an inflation valve 110. The valve body 107 may define a first fluid passageway that connects the pump bulb 106 to the first conduit connector 103. The first fluid passageway may be a cavity that extends through the valve body 107. The first fluid passageway may define a cylindrical cavity having sections with different diameters. The refill valve 108 is disposed within at least one of the sections of the first fluid passageway. The valve body 107 may define a second fluid passageway that connects the pump bulb 106 to the second conduit connector 105. The second fluid passageway may be a cavity that extends through the valve body 107. The second fluid passageway is separate from the first fluid passageway. The second fluid passageway may define a cylindrical cavity having sections with different diameters. The inflation valve 110 is disposed within at least one of the sections of the second fluid passageway.

The refill valve 108 moves within the first fluid passageway between an open position and a closed position (or sealing position). The refill valve 108 does not use a spring to return to the sealing position. The refill valve 108 is moved (in a first direction) to the sealing position when the operator depresses the pump bulb 106 via fluid dynamic forces. By depressing the pump bulb 106, pressure is increased on the downstream side of the refill valve 108, which forces fluid around the refill valve 108 at an elevated velocity which carries the refill valve 108 into the seat, sealing off the flow. Once the flow stops, the pressure increases on the downstream side (e.g., inflation side) and this fluid is pushed into the inflation valve system of the pump assembly 101. Once the patient releases the pump bulb 106, the pump bulb 106 expands back to its home position creating a vacuum. Since there is no longer a spring creating valve crack resistance, the vacuum (negative pressure) pulls the refill valve 108 off its seat (in a second direction opposite to the first direction), allowing fluid to flow freely into the pump bulb 106. Implementations of the refill valve 108 and the valve body 107 defining the first fluid passageway are discussed with reference to FIGS. 4-8.

The inflation valve 110 moves within the second fluid passageway between an open position and a closed position (or sealing position), and a biasing member is used to bias the inflation valve 110 to the sealing position. In some examples, the biasing member is a spring. The inflation valve 110 may provide a reliable seal in order to maintain fluid pressure within the inflatable member 104, but also allow fluid in during inflation of the inflatable member 104. When the patient compresses the pump bulb 106, the pressure increases within the pump bulb 106 and eventually opens the inflation valve 110, thereby allowing fluid to pass over the inflation valve 110. The initial opening of the inflation valve 110 requires compression of the pump bulb 106, resulting in a pressure spike that opens the inflation valve 110. Keeping the inflation valve 110 open is dependent on the pressure differential over the inflation valve seat, which is determined by the application of force by the patient as mentioned above in addition to spring preload/rate and downstream flow resistance. Implementations of the inflation valve 110 and the valve body 107 defining the second fluid passageway are discussed with reference to FIGS. 9-17.

In some examples, the refill valve 108 and/or inflation valve 110 may include a flapper design that includes a wafer of elastomeric seal material sandwiched between two pieces of nitinol, where a check valve pattern is cut into one of the nitinol layers. Implementations of the flapper design are discussed with reference to FIGS. 18-24.

Figure 2:
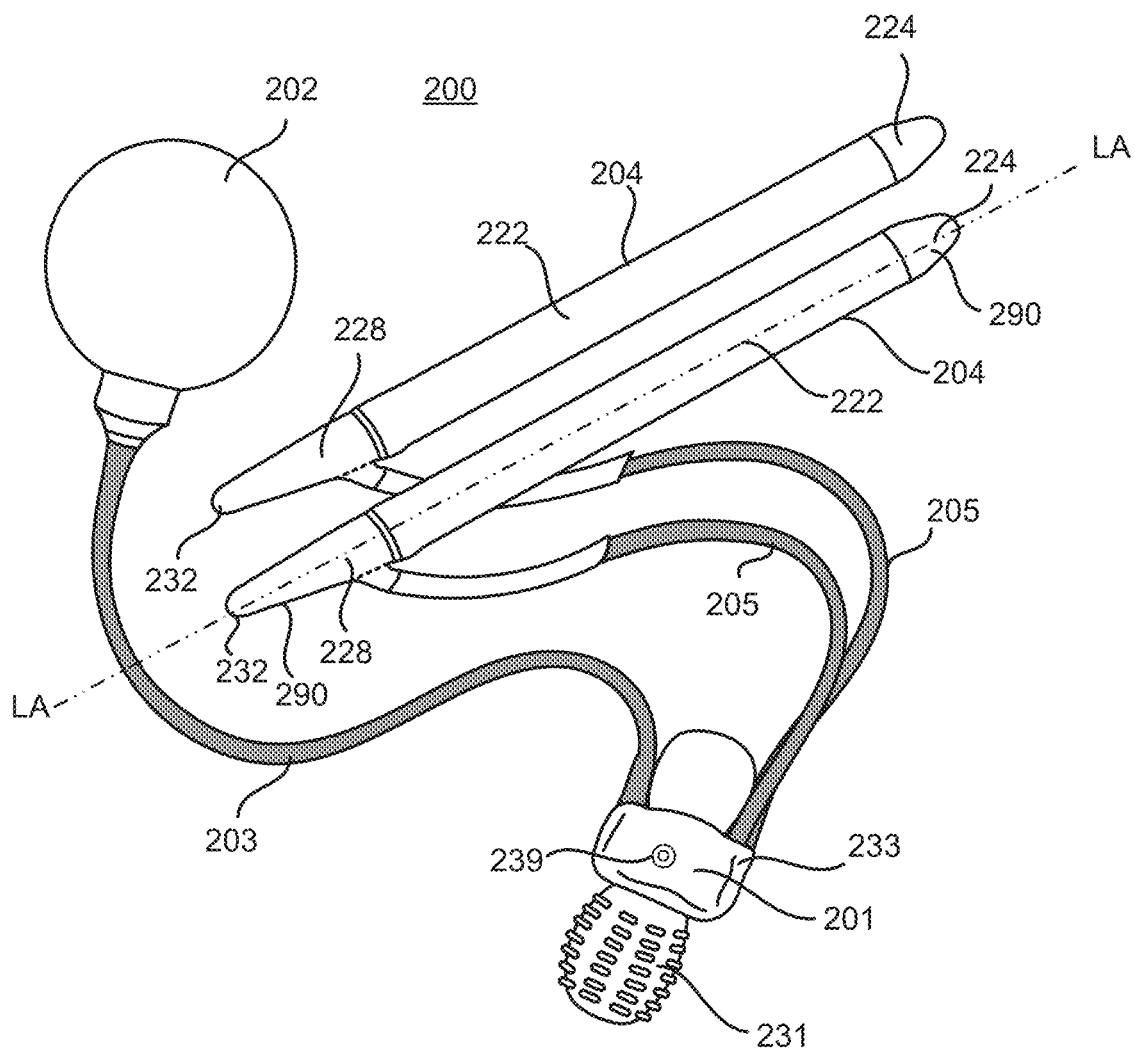
FIG. 2 illustrates a penile prosthesis according to another aspect.
Figure 3:
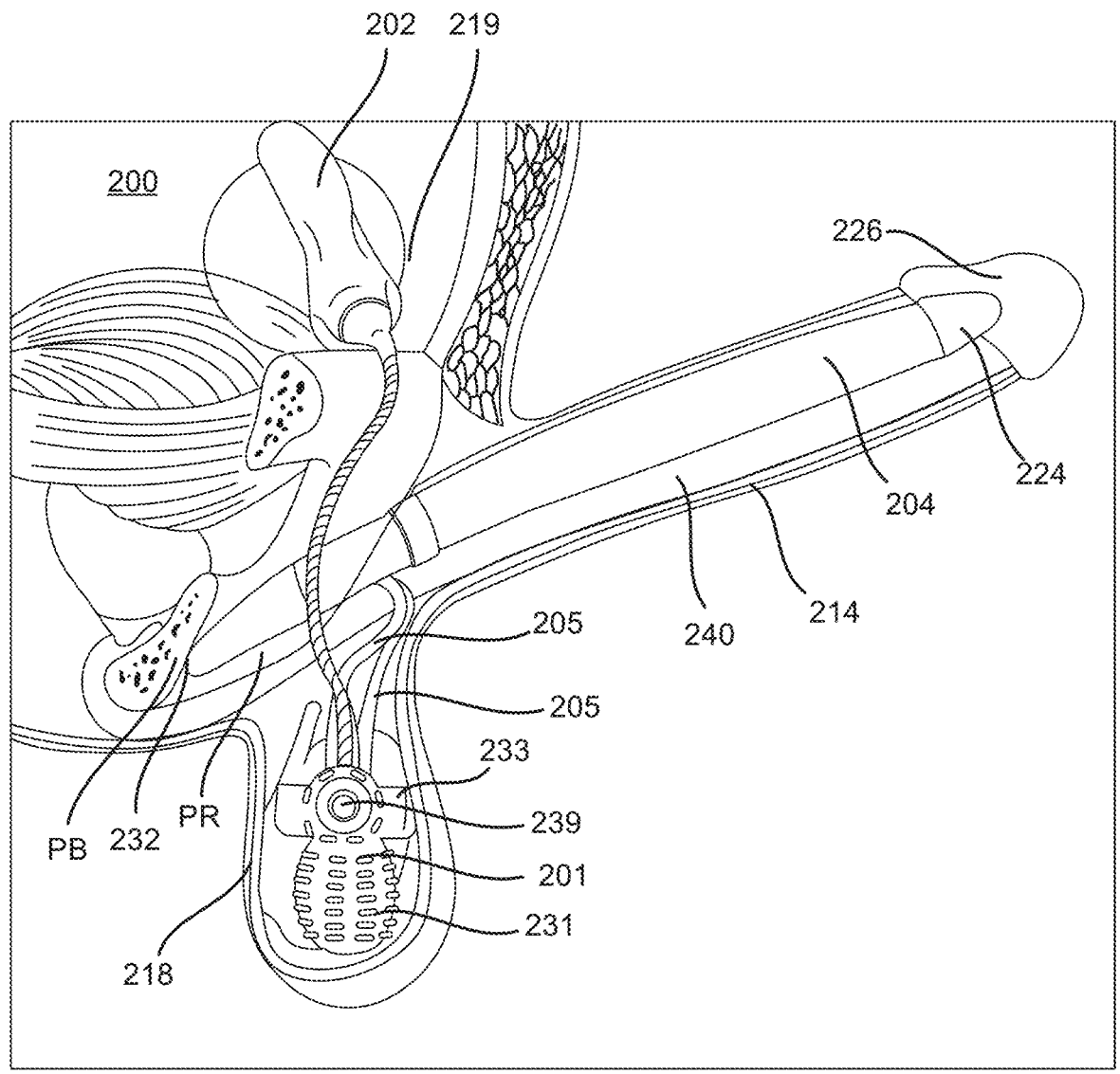
FIG. 3 schematically illustrates a penile prosthesis placed within a body of the user or patient according to an aspect.

FIG. 2 illustrates a penile prosthesis 200 according to an aspect. FIG. 3 schematically illustrates the penile prosthesis 200 placed within a body of the user or patient according to an aspect. The penile prosthesis 200 may include a pair of cylinders 204, and the pair of cylinders or inflatable members 204 are implanted in a penis 214. For example, one of the cylinders 204 may be disposed on one side of the penis 214. The other cylinder 204 (not shown in FIG. 3) of the pair of cylinders may be disposed on the other side of the penis 214. The cylinder 204 may include a first end portion 224, a cavity or inflation chamber 222, and a second end portion 228 having a rear tip 232.

The penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the user's abdomen 219. The inflation chamber or portion 222 of the cylinder 204 may be disposed within the penis 214. The first end portion 224 of the cylinder 204 may be at least partially disposed within the crown portion 226 of the penis 214. The second end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area to prepare the patient to receive the second end portion 228. The surgeon may measure the length of the corpora cavernosae from the incision and the dilated region of the pubic area to determine an appropriate size of the inflatable members or cylinders 204 to implant.

After the patient is prepared, the penile prosthesis 200 is implanted into the patient. The tip of the first end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the tip. The surgeon then inserts the second end portion 228. The surgeon inserts the rear end of the cylinder 204 into the incision and forces the second end portion 228 toward the pubic bone PB until each cylinder 204 is in place.

The pump assembly 201 includes a pump bulb 231, a valve body 233, and a selection member 239. The selection member 239 may be used to select or change the mode in which the pump assembly 201 is in. For example, the selection member 239 may be moved from a first position to a second position to place the device in its deflation mode. The selection member 239 may then be moved back to its first position to place the device in its inflation mode. In some embodiments, the selection member 239 is movable with respect to the valve body 233.

The pump bulb 231 may be squeezed or depressed by the user in order to facilitate the transfer of fluid from the reservoir 202 to the inflatable member 204. For example, in the inflation mode, while the user is operating the pump bulb 231, the pump bulb 231 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 231 to the reservoir 202.

Figure 4A:
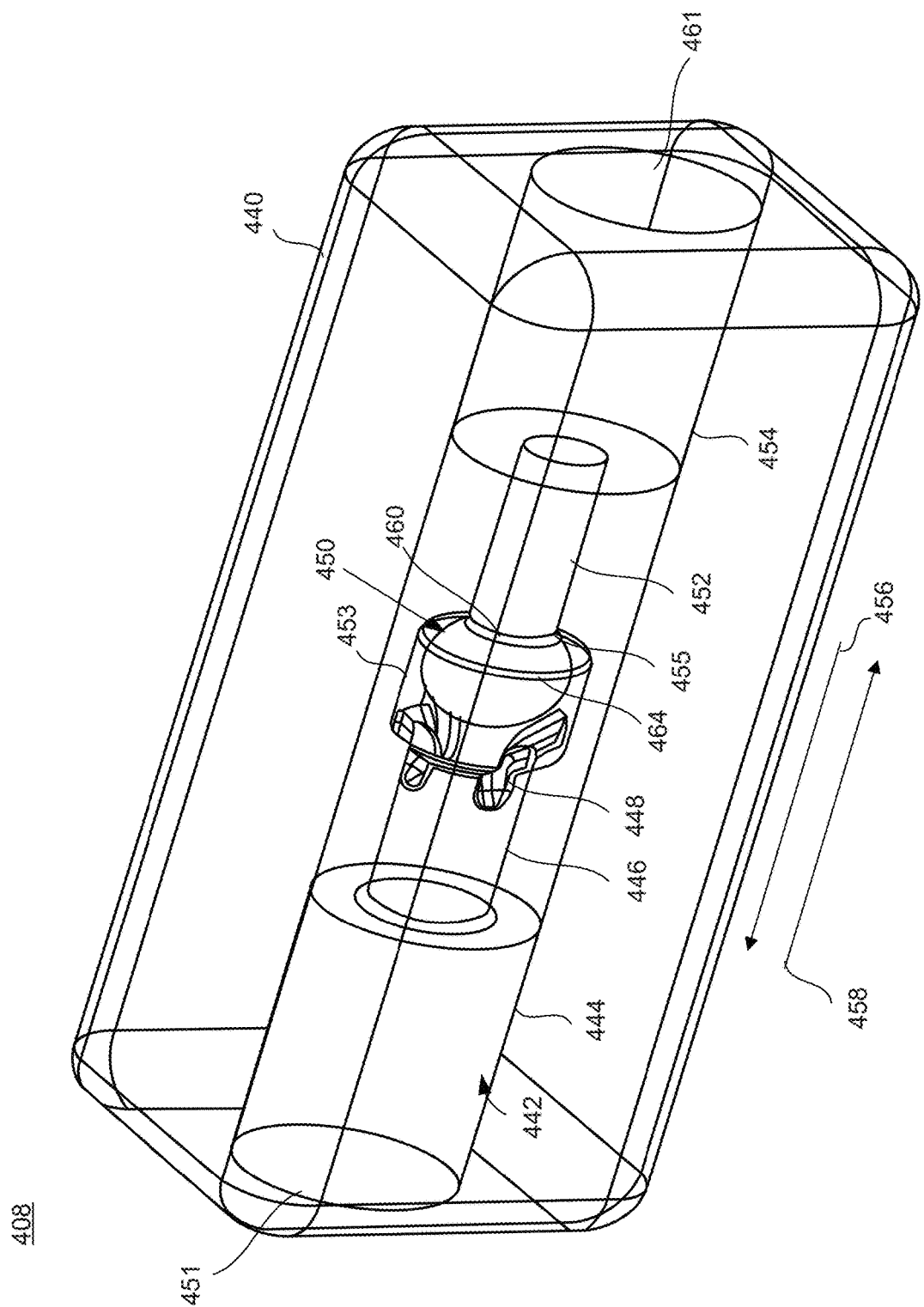
FIG. 4A illustrates a refill valve assembly according to an aspect.
Figure 4B:
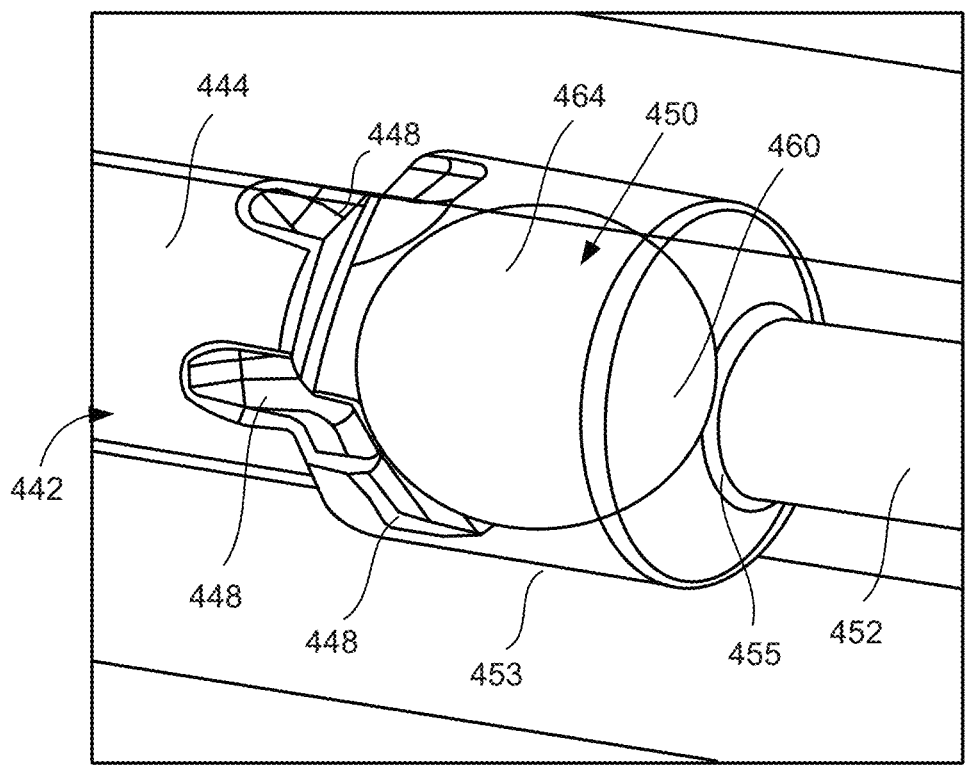
FIG. 4B illustrates a refill valve within a fluid passageway at an open position according to an aspect.
Figure 4C:
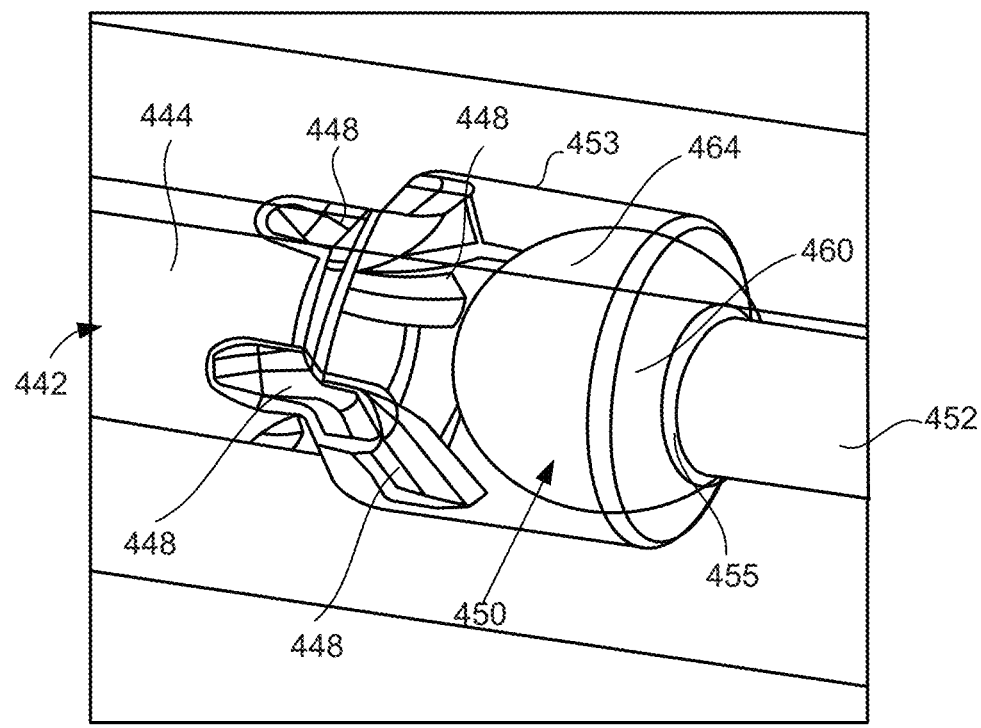
FIG. 4C illustrates the refill valve within the fluid passageway at a closed position according to an aspect.
Figure 4D:
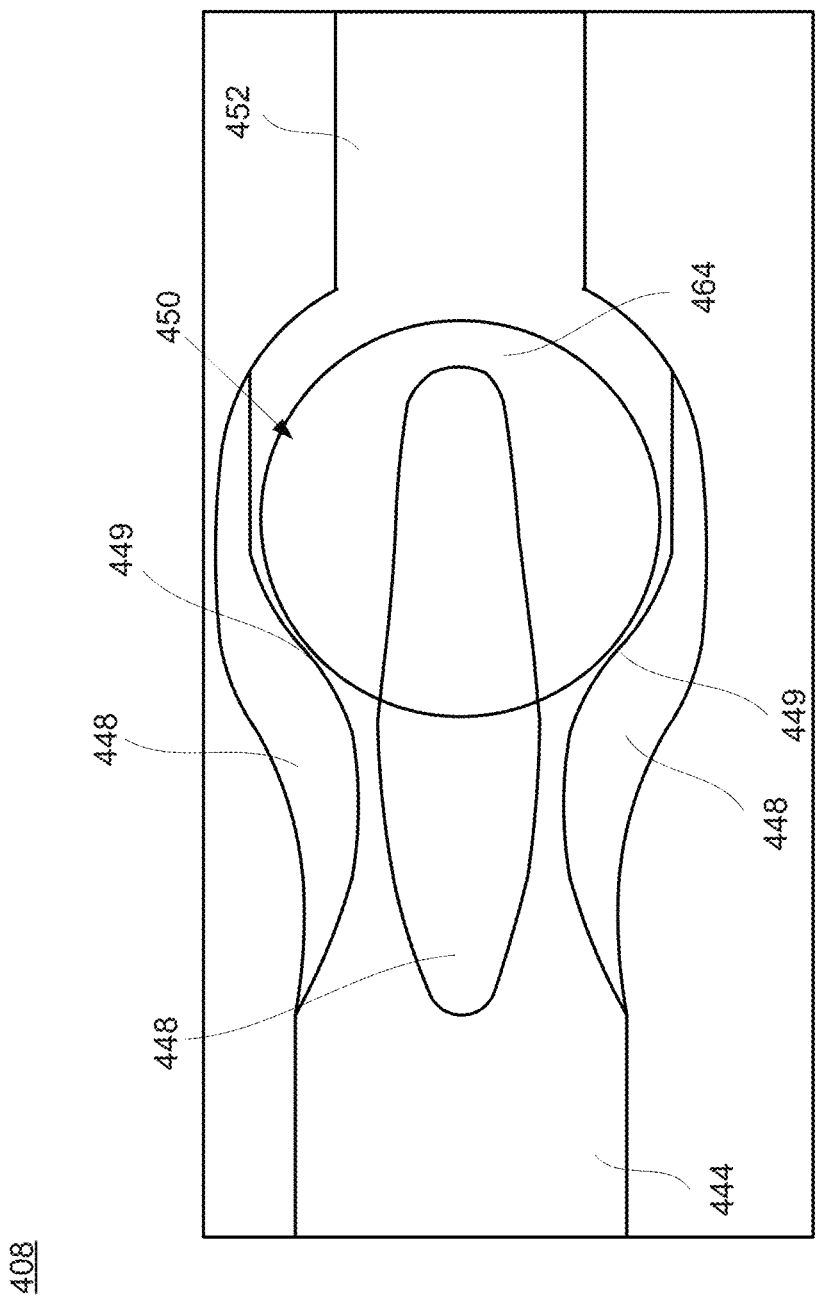
FIG. 4D illustrates a perspective of the refill valve according to an aspect.

FIG. 4A illustrates a refill valve assembly 408 having a valve body 440 defining a fluid passageway 442 and a refill valve 450 disposed within the fluid passageway 442 according to an aspect. FIG. 4B illustrates the refill valve 450 within the fluid passageway 442 at an open position according to an aspect. FIG. 4C illustrates refill valve 450 within the fluid passageway 442 at a closed position according to an aspect. FIG. 4D illustrates a perspective of the refill valve 450 according to an aspect. In some examples, the refill valve 450 is a hydraulic low resistance fluid velocity valve.

The refill valve 450 may include a valve member 464. The valve member 464 may include a three-dimensional round object. In some examples, the valve member 464 includes a round or circular portion. In some examples, as shown in FIGS. 4A-4D, the valve member 464 includes a spherical ball. In some examples, the valve member 464 includes a cylindrical portion. In some examples, the valve member 464 includes one or more surface features to help diffuse the flow of fluid around the refill valve 450. In some examples, the valve member 464 includes a plurality of grooves. In some examples, the valve member 464 includes a plurality of ridges.

The valve body 440 includes a first opening 451 (defined by one end of the valve body 440) and a second opening 461 (defined by the other end of the valve body 440), and the fluid passageway 442 extends between the first opening 451 and the second opening 461. In some examples, the first opening 451 is fluidly coupled to the pump bulb (e.g., 106, 206), and the second opening 461 is fluidly coupled to the reservoir (e.g., 102, 104). When the pump bulb is released from being compressed, a negative force is created, and the negative fluid force pulls the fluid through the fluid passageway 442 in a first direction (around the refill valve 450) in order to fill or refill the pump bulb. When the pump bulb is compressed, a positive fluid force is created, and the positive force moves the valve member 464 in a second direction 458 in order to close the fluid passageway 442 and prevent fluid being leaked back to the reservoir. The valve assembly 408 is devoid a biasing member (e.g., spring) in order to return the valve member 464 to the closed position. Rather, the opening and closing of the valve member 464 are based on fluid dynamic forces through the valve assembly 408.

The valve member 464 moves within the fluid passageway 442 between an open position (as shown in FIG. 4B) and a closed position (as shown in FIG. 4C). In some examples, the entire valve member 464 is disposed within the fluid passageway 442 in either the closed position or the open position. When an operator depresses the pump bulb, the valve member 464 moves in the second direction 458 via fluid dynamic forces. For example, by depressing the pump bulb, pressure is increased on the downstream side (e.g., the left side of the refill valve 450 in FIG. 4A), which forces fluid around the valve member 464 at an elevated velocity which carries the valve member 464 (in the second direction 458) into a seat 455, which seals off the flow through the fluid passageway 442. Once the operator releases the pump bulb, the pump bulb expands back to its home position creating a vacuum. Since there is no longer a spring creating valve crack resistance, the vacuum (negative pressure) pulls the valve member 464 off the seat 455 in the first direction 456, which allows fluid to flow around the valve member 464 (and into pump bulb).

The fluid passageway 442 is a cavity having multiple sizes along a length of the valve body 440. In some examples, the fluid passageway 442 is a cylindrical cavity having segments with different diameters. The fluid passageway 442 may include a first end section 444, and a second end section 454. In some examples, each of the first end section 444 and the second end section 454 is a cylindrical cavity defining a diameter and a length (each segment can have multiple different diameters). The first end section 444 defines the first opening 451, and the second end section 454 defines the second opening 461. In some examples, the second end section 454 has a diameter that is the same as a diameter of the first end section 444. In some examples, the diameter of the second end section 454 is different than the diameter of the first end section 444. In some examples, the length of the first end section 444 is the same as the length of the second end section 454. In some examples, the length of the first end section 444 is different than the length of the second end section 454.

The fluid passageway 442 includes a first flow section 446, a second flow section 452, and a central section 453 disposed between the first flow section 446 and the second flow section 452. In some examples, each of the first flow section 446, the second flow section 452, and the central section 453 is a cylindrical cavity. The valve member 464 is disposed within the central section 453 of the fluid passageway 442, and is designed to not move to other sections of the fluid passageway 442. In some examples, the diameter of the central section 453 is larger than the diameter of the first flow section 446. In some examples, the diameter of the first flow section 446 is the same as the diameter of the central section 453 (where the protrusions 448 restrict movement of the valve member 464 into the first flow section 446). The diameter of the central section 453 is larger than the diameter of the second flow section 452. In some examples, the diameter of the first flow section 446 is larger than the diameter of the second flow section 452. The diameter of the first end section 444 is larger than the diameter of the first flow section 446 (and the diameter of the second flow section 452). The diameter of the second end section 454 is larger than the diameter of the second flow section 452 (and the diameter of the first flow section 446).

In the closed position (as shown in FIG. 4C), the valve member 464 is disposed on the seat 455, and blocks the cavity of the second flow section 452. The seat 455 is defined by the valve body 440 at the end of the second flow section 452 (e.g., the part of the valve body 440 that transitions the diameter of the fluid passageway 442 to a lower amount). The valve member 464 has a size (e.g., a diameter) larger than the diameter of the second flow section 452. As such, when a seat portion 460 of the valve member 464 covers the opening to the second flow section 452, a seal is formed that prevents the flow of fluid over the valve member 464. In some examples, portions of the seat portion 460 are disposed in the second flow section 452. In some examples, the seat portion 460 includes a round portion. In some examples, the seat portion 460 includes a tapered portion.

However, in response to the pump bulb being uncompressed (thereby creating a vacuum or negative pressure), the valve member 464 moves in the first direction 456 until the valve member 464 reaches the open position (as shown in FIG. 4B). In the open position, the valve member 464 contacts a plurality of protrusions 448 that extend from the valve body 440 and into the fluid passageway 442 (at an area proximate to the intersection of the central section 453 and the first flow section 446). In some examples, the protrusions 448 are parts of the valve body 440 that extend into the fluid passageway 442. In some examples, the protrusions 448 are spaced apart from one other around the valve block wall that defines the central section 453. The protrusions 448 extend (at least partially extend) into the central section 453 of the fluid passageway 442. In some examples, the protrusions 448 include four protrusions. However, the embodiments encompass any number of protrusions including one, two, three, or more than four. In some examples, as shown in FIG. 4D, each protrusion 448 includes a curved section 449 that curves into the space of the central section 453 in order to prevent the valve member 464 from further movement in the first direction 456.

The protrusions 448 may prevent the valve member 464 from creating a seal between the valve member 464 and the first flow section 446. For example, the protrusions 448 may prevent the valve member 464 from fully covering the opening of the first flow section 446 thereby blocking the flow of fluid in the first direction 456. The size of the valve member 464 is greater than the size of the opening to the first flow section 446. In some examples, the diameter of the valve member 464 is greater than the diameter of the first flow section 446. When the protrusions 448 contact the valve member 464, the valve member 464 is prevented from covering the opening of the first flow section 446, which creates an empty space between the opening of the first flow section 446 and the valve member 464, which allows the fluid to flow around the valve member 464 and into the first flow section 446.

Figure 5:
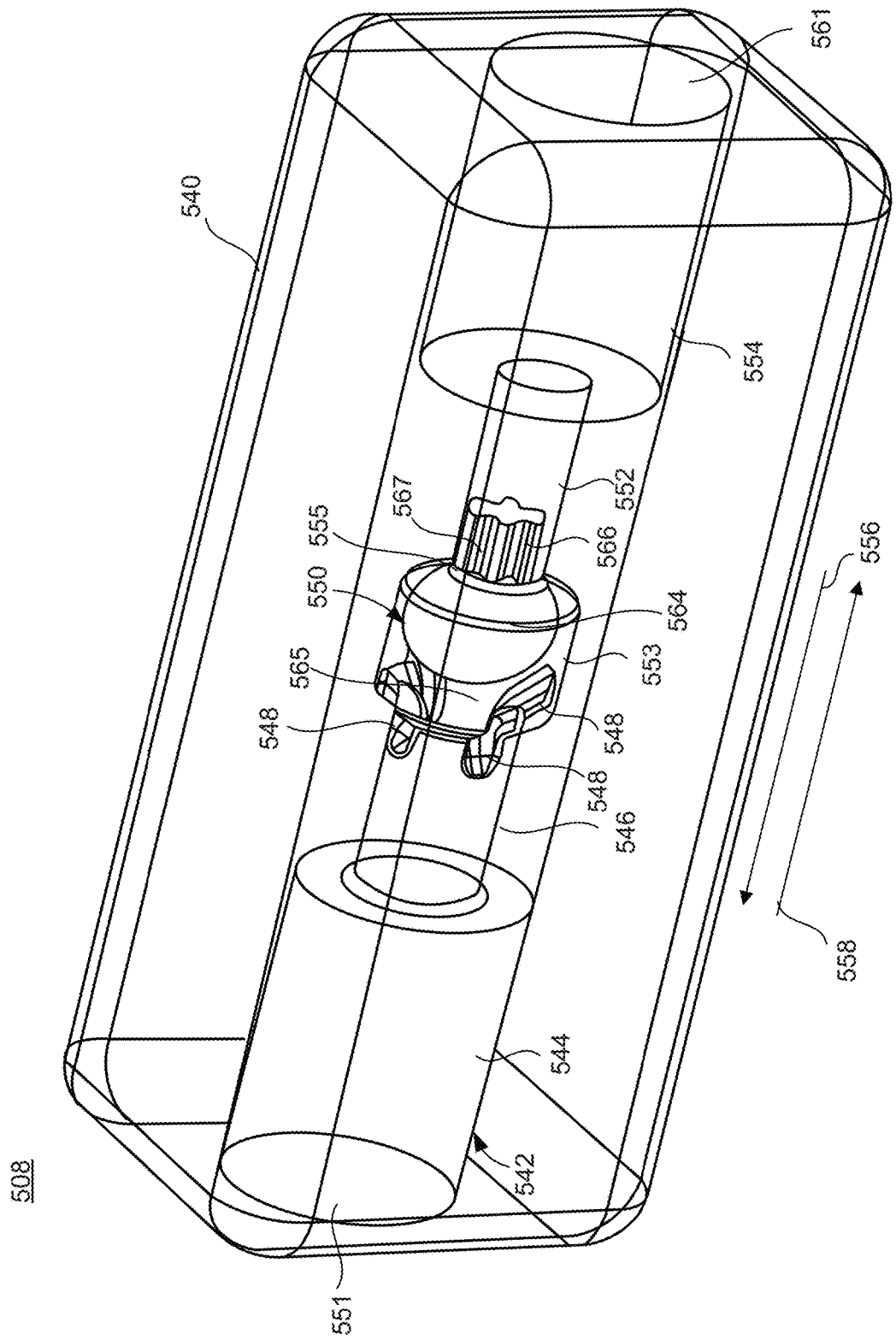
FIG. 5 illustrates a refill valve assembly according to another aspect.

FIG. 5 illustrates a refill valve assembly 508 having a valve body 540 defining a fluid passageway 542 and a refill valve 550 according to another aspect. In some examples, the refill valve 550 is a hydraulic low resistance fluid velocity valve.

The refill valve 550 includes a valve member 564, a first guide member 565, and a second guide member 566. The valve member 564 may include a three-dimensional round object. In some examples, the valve member 564 includes a round or circular portion. In some examples, the valve member 564 includes a spherical ball portion. In some examples, the valve member 564 includes a cylindrical portion. In some examples, the valve member 564 includes one or more surface features to help diffuse the flow of fluid around the valve member 564. In some examples, the valve member 564 includes a plurality of grooves. In some examples, the valve member 564 includes a plurality of ridges.

The first guide member 565 and the second guide member 566 may extend on opposite sides of the valve member. For example, the first guide member 565 may extend from a first side of the valve member 564 in a first direction 556. The second guide member 566 may extend from a second side of the valve member 564 in a second direction 558. In some examples, the first direction 556 is opposite to the second direction 558. In some examples, the first guide member 565, the valve member 564, and the second guide member 566 are integrally-formed with respect to each other (e.g., comprise a single piece of material). In other examples, the first guide member 565, the valve member 564, and the second guide member 566 are separate components that are coupled together. The first guide member 565 and the second guide member 566 may help to stabilize the valve member 564 as the valve member 564 moves between the open position and the closed position.

The first guide member 565 may include a cylindrical member that defines a length and a diameter. In some examples, the surface of the first guide member 565 is smooth (e.g., devoid of surface features). In some examples, the first guide member 565 may include one or more surface features (e.g., ridges, protrusions, grooves). The second guide member 566 may include a cylindrical member that defines a length and a diameter. In some examples, the second guide member 566 includes a fluted cylindrical member. In some examples, the second guide member 566 includes a plurality of grooves 567. The grooves 567 may be spaced apart around the cylinder's surface and are orientated in a direction parallel to the length of the second guide member 566. In some examples, the grooves 567 extend the entire length of the second guide member 566. The grooves 567 may help diffuse the flow of fluid through the refill valve 550. In some examples, the length of the first guide member 565 is substantially equal to the length of the second guide member 566. In some examples, the length of the first guide member 565 is different than the length of the second guide member 566. In some examples, the diameter of the first guide member 565 may be the same as the diameter of the second guide member. In some examples, the diameter of the first guide member 565 is different than the length of the second guide member 566.

The valve body 540 includes a first opening 551 and a second opening 561, and the fluid passageway 542 extends between the first opening 551 and the second opening 561. In some examples, the first opening 551 is fluidly coupled to the pump bulb (e.g., 106, 206), and the second opening 561 is fluidly coupled to the reservoir (e.g., 102, 104). When the pump bulb is released from compressed, a negative force is created, and the negative fluid force pulls the fluid through the fluid passageway 542 in a first direction 556 (around the refill valve 550) in order to fill or refill the pump bulb. When the pump bulb is compressed, a positive fluid force is created, and the positive force moves the valve member 564 in the second direction 558 in order to close the fluid passageway 542 and prevent fluid being leaked back to the reservoir. The valve assembly 508 is devoid a biasing member (e.g., spring) in order to return the refill valve 550 to the closed position. Rather, the opening and closing of the refill valve 550 are based on fluid dynamic forces through the valve assembly 508.

The fluid passageway 542 is a cavity in the valve body 540. The fluid passageway 542 has multiple sizes along a length of the valve body 540. In some examples, the fluid passageway 542 is a cylindrical cavity having segments with different diameters. The fluid passageway 542 may include a first end section 544 (defining the first opening 551), a second end section 554 (defining the second opening 561), a first flow section 546, a second flow section 552, and a central section 553. The sections of the fluid passageway 542 may include any of the features described with reference to FIGS. 4A-4E.

The valve member 564 is disposed within the central section 553 and is designed to not move to other sections of the fluid passageway 542. The size of the valve member 564 may be less than the diameter of the central section 553, and the length of the valve member 564 may be less than a length of the central section 553. The overall length of the refill valve 550 (e.g., measured from the end of the first guide member 565 to the end of the second guide member 566) may be greater than the length of the central section 553. The diameter of the first guide member 565 may be less than the diameter of the first flow section 546 such that at least a portion of the first guide member 565 can extend into the first flow section 546. The diameter of the second guide member 566 may be less than the diameter of the second flow section 552 such that at least a portion of the second guide member 566 can extend into the second flow section 552.

In the closed position (as shown in FIG. 5), the valve member 564 is disposed on the seat 555, and blocks the opening to the cavity of the second flow section 452. The seat 555 is defined by the valve body 540 at the end of the second flow section 552 (e.g., the part of the valve body 540 that transitions the diameter of the fluid passageway 542 to a lower amount). The valve member 564 has a size (e.g., a diameter) larger than the diameter of the second flow section 552. As such, when a seat portion of the valve member 564 covers the opening to the second flow section 552, a seal is formed that prevents the flow of fluid over the valve member 564. In the closed position, the entire second guide member 566 is disposed in the second flow section 552. In the closed position, only a portion of the first guide member 565 is disposed in the first flow section 546.

In response to the pump bulb being uncompressed (thereby creating a vacuum or negative pressure), the refill valve 550 moves in the first direction 556 until the valve member 564 reaches the open position. In the open position, the valve member 564 contacts a plurality of protrusions 548 that extend from the valve body 540 and into the fluid passageway 542 (at an area proximate to the intersection of the central section 553 and the first flow section 546). In some examples, the protrusions 548 are parts of the valve body 540 that extend into the fluid passageway 542. The protrusions 548 may include any of the features described with reference to FIGS. 4A-4D. When the protrusions 548 contact the valve member 564, the valve member 564 is prevented from covering the opening of the first flow section 546, which creates an empty space between the opening of the first flow section 546 and the valve member 564, which allows the fluid to flow around the valve member 564 and into the first flow section 546. The diameter of the first guide member 565 is smaller than the space between the protrusions 548 such that the first guide member 565 can slide between the protrusions 548 allow the refill valve 550 to move to the open position.

Figure 6:
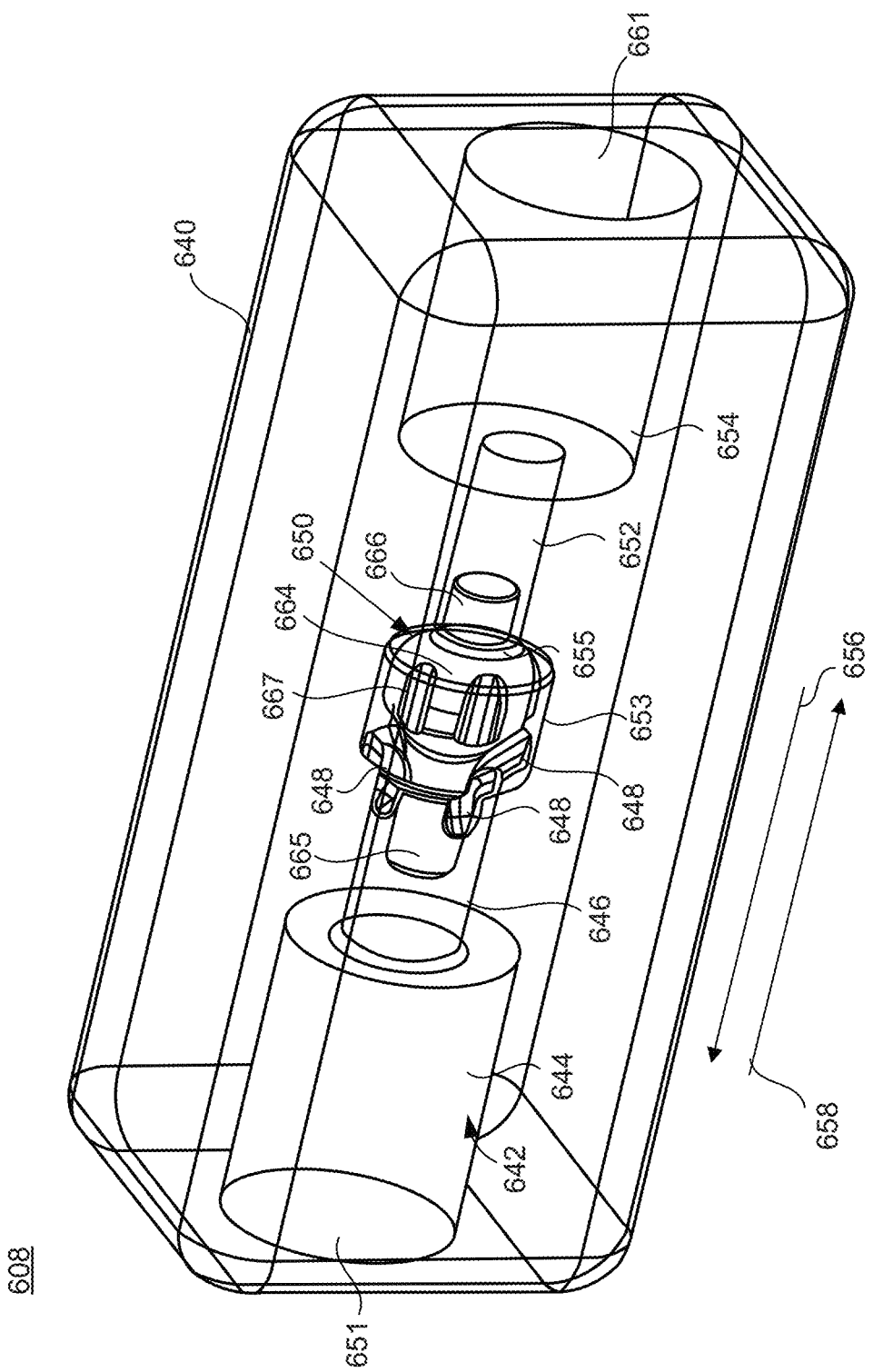
FIG. 6 illustrates a refill valve assembly according to another aspect.

FIG. 6 illustrates a refill valve assembly 608 having a valve body 640 defining a fluid passageway 642 and a refill valve 650 according to another aspect. In some examples, the refill valve 650 is a hydraulic low resistance fluid velocity valve.

The refill valve 650 includes a valve member 664, a first guide member 665, and a second guide member 666. The valve member 664 may include a three-dimensional round object. In some examples, the valve member 664 includes a round or circular portion. In some examples, the valve member 664 includes a tapered portion. In some examples, the valve member 664 includes a tapered ball portion. The valve member 664 includes a plurality of grooves 667. The grooves 667 may be spaced around the cylinder's surface, and are orientated in a direction parallel to the length of the valve member 664 (or in a direction parallel to a first direction 656 or second direction 658). The grooves 667 may be surface features that help to fuse the flow of fluid around the valve member 664 in the first direction 656.

The first guide member 665 and the second guide member 666 may extend on opposite sides of the valve member 664. The first guide member 665 may extend from a first side of the valve member 664 in the first direction 656. The second guide member 666 may extend from a second side of the valve member 664 in the second direction 658. In some examples, the first direction 656 is opposite to the second direction 658. In some examples, the first guide member 665, the valve member 664, and the second guide member 666 are integrally-formed with respect to each other (e.g., comprise a single piece of material). In other examples, the first guide member 665, the valve member 664, and the second guide member 666 are separate components that are coupled together. The first guide member 665 and the second guide member 666 may help to stabilize the valve member 664 as the valve member 664 moves between the open position and the closed position.

The first guide member 665 may include a cylindrical member that defines a length and a diameter. In some examples, the surface of the first guide member 665 is smooth (e.g., devoid of surface features such as ridges, protrusions, grooves). The second guide member 666 may include a cylindrical member that defines a length and a diameter. In some examples, the surface of the second guide member 666 is smooth (e.g., devoid of surface features such as ridges, protrusions, grooves). The length of the first guide member 665 may be larger than the length of the second guide member 666. In some examples, the diameter of the first guide member 665 and the diameter of the second guide member 666 is the same. In some examples, the diameter of the first guide member 665 and the diameter of the second guide member 666 are different.

The valve body 640 includes a first opening 651 and a second opening 661, and the fluid passageway 642 extends between the first opening 651 and the second opening 661. In some examples, the first opening 651 is fluidly coupled to the pump bulb (e.g., 106, 206), and the second opening 661 is fluidly coupled to the reservoir (e.g., 102, 104). When the pump bulb is released from being compressed, a negative force is created, and the negative fluid force pulls the fluid through the fluid passageway 642 in a first direction 656 (around the refill valve 650) in order to fill or refill the pump bulb. When the pump bulb is compressed, a positive fluid force is created, and the positive force moves the valve member 664 in the second direction 658 in order to close the fluid passageway 642 and prevent fluid being leaked back to the reservoir. The valve assembly 608 is devoid a biasing member (e.g., spring) in order to return the refill valve 650 to the closed position. Rather, the opening and closing of the refill valve 650 are based on fluid dynamic forces through the valve assembly 608.

The fluid passageway 642 is a cavity in the valve body 640. The fluid passageway 642 has multiple sizes along a length of the valve body 640. In some examples, the fluid passageway 642 is a cylindrical cavity having segments with different diameters. The fluid passageway 642 may include a first end section 644 (defining the first opening 651), a second end section 654 (defining the second opening 661), a first flow section 646, a second flow section 652, and a central section 653. The sections of the fluid passageway 642 may include any of the features described with reference to FIGS. 4A-4E.

The valve member 664 is disposed within the central section 653 and is designed to not move to other sections of the fluid passageway 642. The size of the valve member 664 may be less than the diameter of the central section 653, and the length of the valve member 664 may be less than a length of the central section 653. The overall length of the refill valve 650 (e.g., measured from the end of the first guide member 665 to the end of the second guide member 666) may be greater than the length of the central section 653. The diameter of the first guide member 665 may be less than the diameter of the first flow section 646 such that at least a portion of the first guide member 665 can extend into the first flow section 646. The diameter of the second guide member 666 may be less than the diameter of the second flow section 652 such that at least a portion of the second guide member 666 can extend into the second flow section 652.

In the closed position (as shown in FIG. 6), the valve member 664 is disposed on the seat 655, and blocks the opening to the cavity of the second flow section 652. The seat 655 is defined by the valve body 640 at the end of the second flow section 652 (e.g., the part of the valve body 640 that transitions the diameter of the fluid passageway 642 to a lower amount). The valve member 664 has a size (e.g., a diameter) larger than the diameter of the second flow section 652. As such, when a seat portion of the valve member 664 covers the opening to the second flow section 652, a seal is formed that prevents the flow of fluid over the valve member 664. In the closed position, the entire second guide member 666 is disposed in the second flow section 652. In the closed position, only a portion of the first guide member 665 is disposed in the first flow section 646. In some examples, in the closed position, a majority of the first guide member 665 is still disposed in the first flow section 646.

In response to the pump bulb being uncompressed (thereby creating a vacuum or negative pressure), the refill valve 650 moves in the first direction 656 until the valve member 664 reaches the open position. In the open position, the valve member 664 contacts a plurality of protrusions 648 that extend from the valve body 640 and into the fluid passageway 642 (at an area proximate to the intersection of the central section 653 and the first flow section 646). In some examples, the protrusions 648 are parts of the valve body 640 that extend into the fluid passageway 642. The protrusions 648 may include any of the features described with reference to FIGS. 4A-4D. When the protrusions 648 contact the valve member 664, the valve member 664 is prevented from covering the opening of the first flow section 646, which creates an empty space between the opening of the first flow section 646 and the valve member 664, which allows the fluid to flow around the valve member 664 and into the first flow section 646. The diameter of the first guide member 665 is smaller than the space between the protrusions 648 such that the first guide member 665 can slide between the protrusions 648 allow the refill valve 650 to move to the open position.

Figure 7:
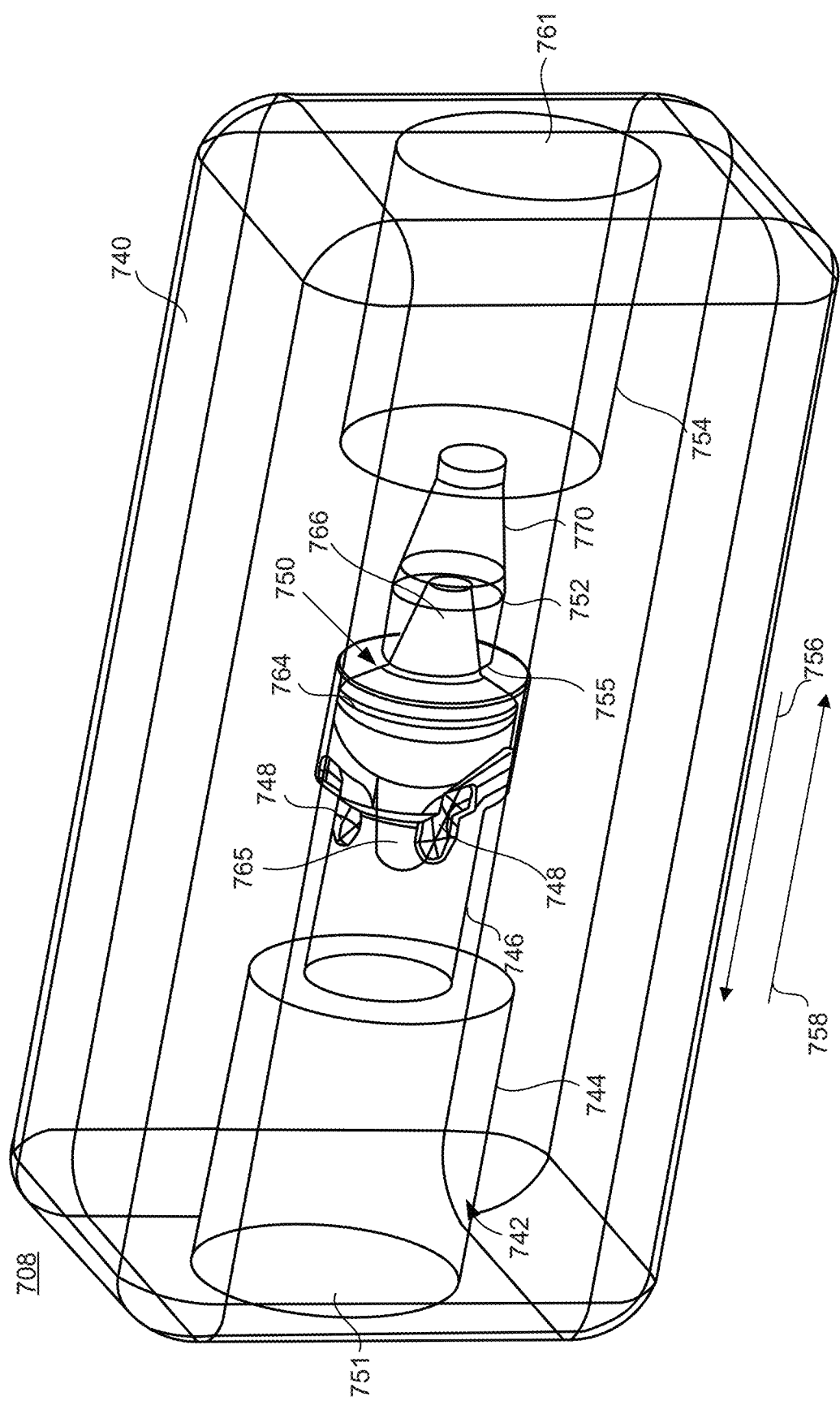
FIG. 7 illustrates a refill valve assembly according to another aspect.
Figure 8:
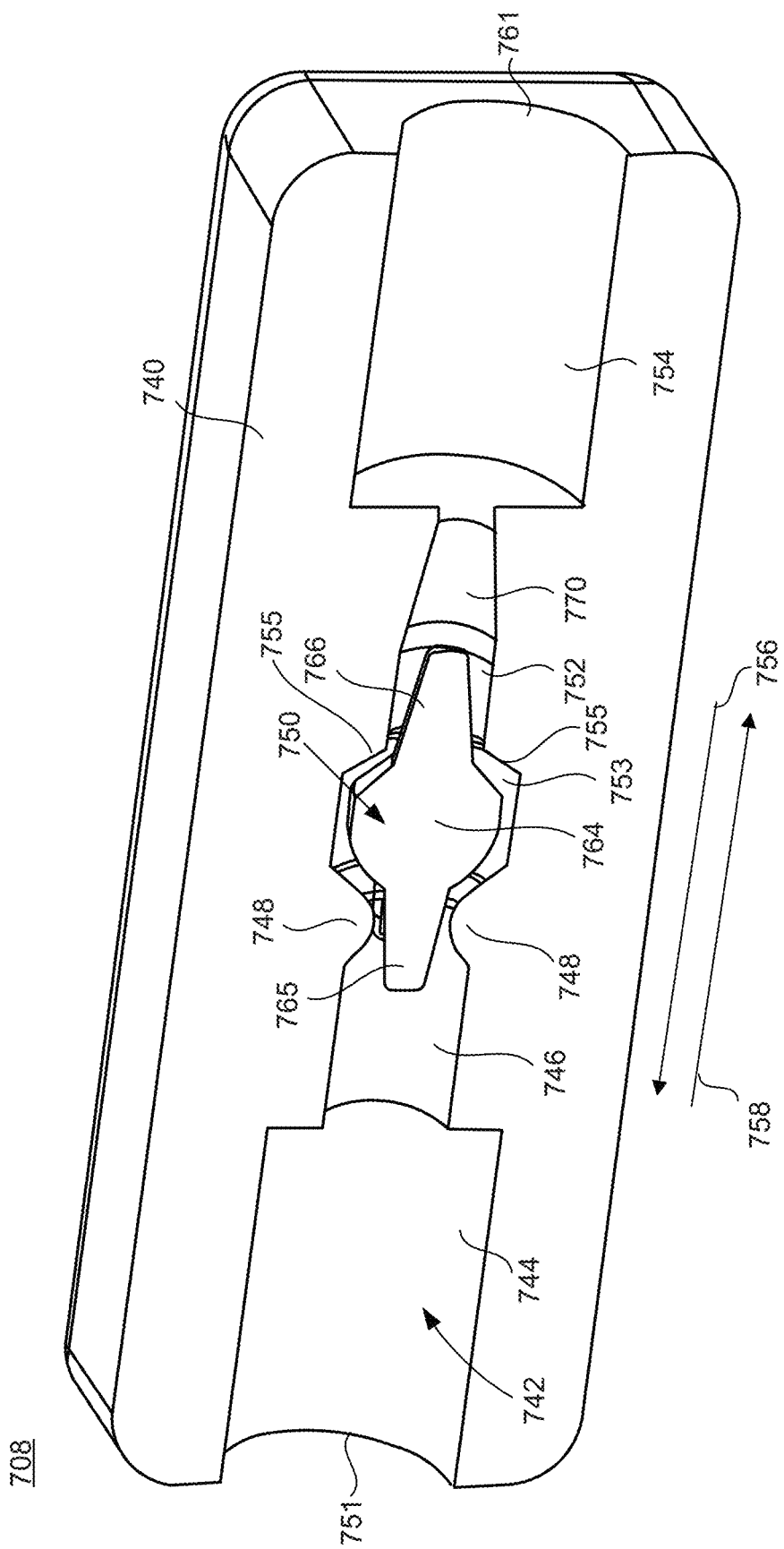
FIG. 8 illustrates a cross-sectional view of the refill valve assembly of FIG. 7 according to an aspect.

FIG. 7 illustrates a refill valve assembly 708 having a valve body 740 defining a fluid passageway 742 and a refill valve 750 according to another aspect. FIG. 8 illustrates a cross-sectional view of the refill valve assembly 708 according to an aspect. In some examples, the refill valve 750 is a hydraulic low resistance fluid velocity valve.

Referring to FIGS. 7 and 8, the refill valve 750 includes a valve member 764, a first guide member 765, and a second guide member 766. The valve member 764 may include a three-dimensional object. In some examples, the valve member 764 includes a curved portion. In some examples, the valve member 764 includes a round portion. In some examples, the surface of the valve member 764 is relatively smooth or devoid of surface features (e.g., ridges, grooves, protrusions).

The first guide member 765 and the second guide member 766 may extend on opposite sides of the valve member 764. The first guide member 765 may extend from a first side of the valve member 764 in the first direction 756. The second guide member 766 may extend from a second side of the valve member 764 in the second direction 758. The first direction 756 is opposite to the second direction 758. In some examples, the first guide member 765, the valve member 764, and the second guide member 766 are integrally-formed with respect to each other (e.g., comprise a single piece of material). In other examples, the first guide member 765, the valve member 764, and the second guide member 766 are separate components that are coupled together. The first guide member 765 and the second guide member 766 may help to stabilize the valve member 764 as the valve member 764 moves between the open position and the closed position.

The first guide member 765 may include a conical member. In some examples, the surface of the first guide member 765 is smooth (e.g., devoid of surface features such as ridges, protrusions, grooves). The second guide member 766 may include a conical member. In some examples, the surface of the second guide member 766 is smooth (e.g., devoid of surface features such as ridges, protrusions, grooves). In some examples, the length of the second guide member 766 may be same as the length of the first guide member 765. In some examples, the length of the second guide member 766 is different than the length of the first guide member 765.

The valve body 740 includes a first opening 751 and a second opening 761, and the fluid passageway 742 extends between the first opening 751 and the second opening 761. In some examples, the first opening 751 is fluidly coupled to the pump bulb (e.g., 106, 206), and the second opening 761 is fluidly coupled to the reservoir (e.g., 102, 104). When the pump bulb is released from being compressed, a negative force is created, and the negative fluid force pulls the fluid through the fluid passageway 742 in a first direction 756 (around the refill valve 750) in order to fill or refill the pump bulb. When the pump bulb is compressed, a positive fluid force is created, and the positive force moves the valve member 764 in the second direction 758 in order to close the fluid passageway 742 and prevent fluid being leaked back to the reservoir. The valve assembly 708 is devoid a biasing member (e.g., spring) in order to return the refill valve 750 to the closed position. Rather, the opening and closing of the refill valve 750 are based on fluid dynamic forces through the valve assembly 708.

The fluid passageway 742 is a cavity in the valve body 740. The fluid passageway 742 has multiple sizes along a length of the valve body 740. In some examples, the fluid passageway 742 is a cylindrical cavity having segments with different diameters. The fluid passageway 742 may include a first end section 744 (defining the first opening 751), a second end section 754 (defining the second opening 761), a first flow section 746, a second flow section 752, and a central section 753. The sections of the fluid passageway 742 may include any of the features described with reference to FIGS. 4A-4E. As shown in FIG. 7, the second flow section 752 may include a tapered portion 770 that tapers towards the second end section 754.

The valve member 764 is disposed within the central section 753 and is designed to not move to other sections of the fluid passageway 742. The size of the valve member 764 may be less than the diameter of the central section 753, and the length of the valve member 764 may be less than a length of the central section 753. The overall length of the refill valve 750 (e.g., measured from the end of the first guide member 765 to the end of the second guide member 766) may be greater than the length of the central section 753. The diameter of the first guide member 765 may be less than the diameter of the first flow section 746 such that at least a portion of the first guide member 765 can extend into the first flow section 746. The diameter of the second guide member 766 may be less than the diameter of the second flow section 752 such that at least a portion of the second guide member 766 can extend into the second flow section 752.

In the closed position, the valve member 764 is disposed on a tapered valve seat 755, and blocks the opening to the cavity of the second flow section 752. The tapered valve seat 755 is defined by the valve body 740 at the end of the second flow section 752 (e.g., the part of the valve body 740 that transitions the diameter of the fluid passageway 742 to a lower amount). The valve member 764 has a size (e.g., a diameter) larger than the diameter of the second flow section 752. As such, when a seat portion (which may have a tapering that matches the tapering of the tapered valve seat 755) of the valve member 764 covers the opening to the second flow section 752, a seal is formed that prevents the flow of fluid over the valve member 764. In the closed position, the entire second guide member 766 is disposed in the second flow section 752. In the closed position, only a portion of the first guide member 765 is disposed in the first flow section 746.

In response to the pump bulb being uncompressed (thereby creating a vacuum or negative pressure), the refill valve 750 moves in the first direction 756 until the valve member 764 reaches the open position. In the open position, the valve member 764 contacts a plurality of protrusions 748 that extend from the valve body 740 and into the fluid passageway 742 (at an area proximate to the intersection of the central section 753 and the first flow section 746). In some examples, the protrusions 748 are parts of the valve body 740 that extend into the fluid passageway 742. The protrusions 748 may include any of the features described with reference to FIGS. 4A-4D. When the protrusions 748 contact the valve member 764, the valve member 764 is prevented from covering the opening of the first flow section 746, which creates an empty space between the opening of the first flow section 746 and the valve member 764, which allows the fluid to flow around the valve member 764 and into the first flow section 746. The diameter of the first guide member 765 is smaller than the space between the protrusions 748 such that the first guide member 765 can slide between the protrusions 748 allow the refill valve 750 to move to the open position.

Figure 9:
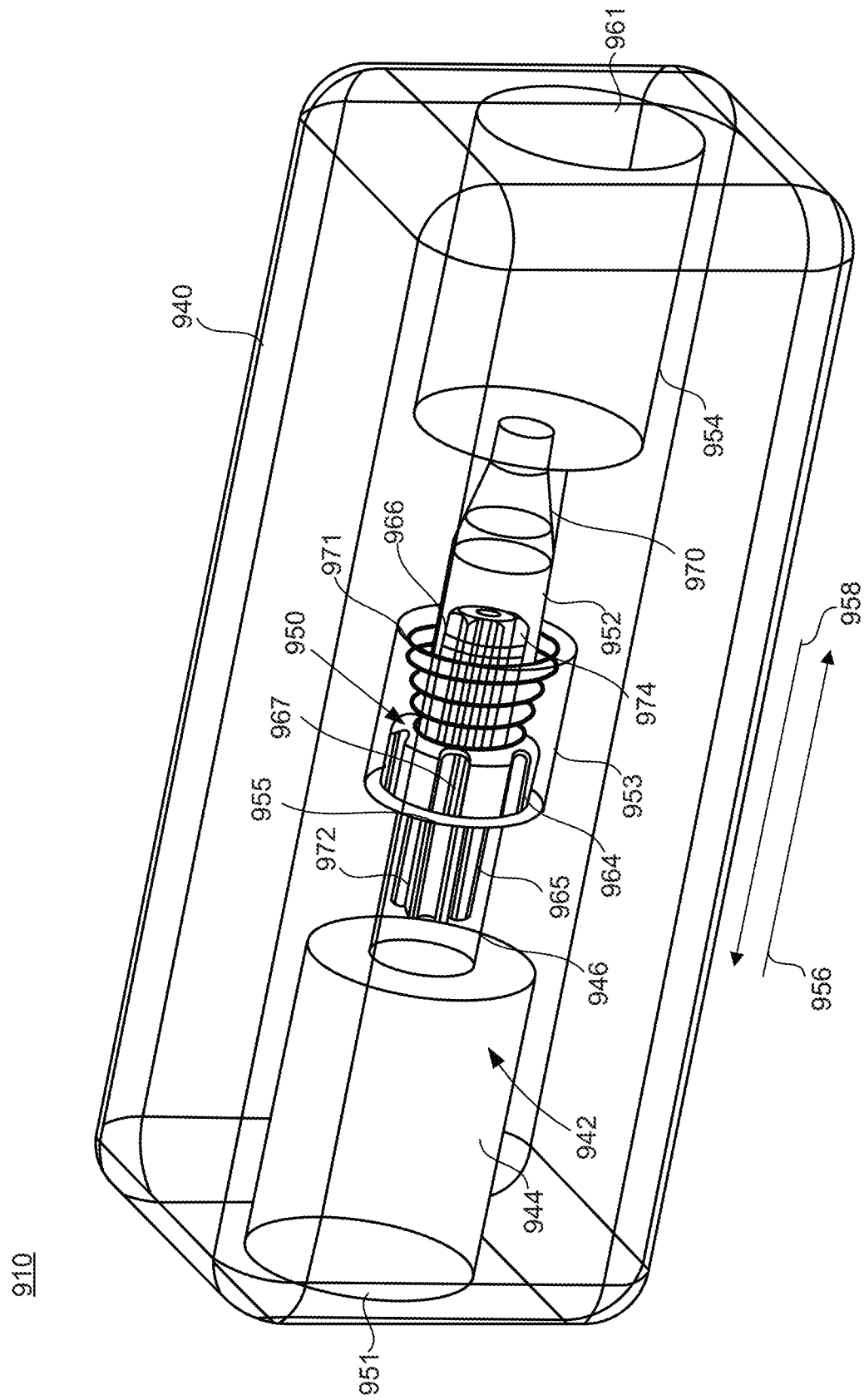
FIG. 9 illustrates an inflation valve assembly according to an aspect.

FIG. 9 illustrates an inflation valve assembly 910 having a valve body 940 defining a fluid passageway 942 and an inflation valve 950 disposed within the fluid passageway 942 according to an aspect. In some examples, the inflation valve 950 is a low resistance inflation valve. When the pump bulb is compressed, pressure increases in the pump bulb, and the inflation valve 950 opens and allows fluid to flow from the pump bulb to the inflatable member (in a first direction 956). When the pressure in the pump bulb decreases below a threshold level, the inflation valve 950 closes and blocks fluid from being transferred from the inflatable member back to the pump bulb (in a second direction 958).

In some examples, the inflation valve 950 is a cylindrical fluted poppet. In some examples, the inflation valve 950 includes a valve member 964, a first guide member 965, and a second guide member 966. The valve member 964 is a three-dimensional object having one or more curved surfaces. In some examples, as shown in FIG. 9, the valve member 964 is a solid cylinder. The valve member 964 may define a plurality of grooves 967. The grooves 967 may be defined on the cylinder's surface. In some examples, the grooves 967 may be spaced around the cylinder's surface and orientated in a direction parallel to the fluid flow path. In some examples, the grooves 967 extend the entire length of the valve member 964. The grooves 967 may help diffuse the flow of fluid around the valve member 964.

The first guide member 965 and the second guide member 966 may extend on opposite ends of the valve member 964. For example, the first guide member 965 may extend from one end of the valve member 964 in the second direction 958. The second guide member 966 may extend from the other end of the valve member 964 in the first direction 956. The first direction 956 is opposite to the second direction 958. In some examples, the first guide member 965, the valve member 964, and the second guide member 966 are integrally-formed with respect to each other (e.g., comprise a single piece of material). In other examples, the first guide member 965, the valve member 964, and the second guide member 966 are separate components that are coupled together. The first guide member 965 and the second guide member 966 may help to stabilize the valve member 964 as the valve member 964 moves between the open position and the closed position.

The first guide member 965 may include a cylindrical member. The first guide member 965 may include a plurality of grooves 972. The grooves 972 may be spaced apart around the cylinder's surface and orientated in a direction parallel to a central axis of the first guide member 965. In some examples, the grooves 972 extend the entire length of the first guide member 965. The second guide member 966 may include a cylindrical member. The second guide member 966 may include a plurality of grooves 974. The grooves 974 may be spaced apart around the cylinder's surface and orientated in a direction parallel to a central axis of the second guide member 966. In some examples, the grooves 974 extend the entire length of the second guide member 966. The grooves 972 and the grooves 974 may help diffuse the flow of fluid around the inflation valve 950. In some examples, the length of the first guide member 965 is substantially equal to the length of the second guide member 966. In some examples, the length of the first guide member 965 is different than the length of the second guide member 966. In some examples, the diameter of the first guide member 965 may be the same as the diameter of the second guide member 966. In some examples, the diameter of the first guide member 965 is different than the diameter of the second guide member 966.

The valve body 940 defines a first opening 951 and a second opening 961, and the fluid passageway 942 extends between the first opening 951 and the second opening 961. The first opening 951 is fluidly coupled to the pump bulb (e.g., 106, 206), and the second opening 961 is fluidly coupled to the inflatable member (e.g., 104, 204).

The fluid passageway 942 is a cavity in the valve body 940. The fluid passageway 942 has multiple sizes along a length of the valve body 940. In some examples, the fluid passageway 942 is a cylindrical cavity having segments with different diameters. The fluid passageway 942 may include a first end section 944 (defining the first opening 951), a second end section 954 (defining the second opening 961), a first flow section 946, a second flow section 952, and a central section 953. The second flow section 952 may include a tapered portion 970. The sections of the fluid passageway 942 may include any of the features described with reference to the previous figures.

The valve member 964 and the biasing member 971 are disposed within the central section 953, and the valve member 964 is biased to the closed (or sealed) position by the biasing member 971. One end of the biasing member 971 contacts (or is coupled to) the valve member 964 and the other end of the biasing member 971 contacts (or is coupled to) the portion of the valve body 940 that defines the end of the central section 953. In some examples, the biasing member 971 is a spring having coils. In the closed position, at least a portion of the second guide member 966 extends through the coils. In some examples, the coils increasingly become larger in the first direction 956.

In the closed position, the valve member 964 is disposed over the opening to the central section 953, thereby blocking the fluid passageway 942. For example, the valve member 964 is disposed on a valve seat 955, and blocks the fluid passageway 942 at intersection of the first flow section 946 and the central section 953. In some examples, the valve seat 955 is defined by the valve body 940 at the intersection of the first flow section 946 and the central section 953. In some examples, the valve seat 955 is tapered. When the operator compresses the pump bulb, the pressure increases within the pump bulb, and moves the valve member 964 in the first direction 956. Movement of the valve member 964 in the first direction 956 compresses the biasing member 971 and unblocks the fluid passageway 942, thereby allowing fluid to pass over the inflation valve 950. The initial opening of the inflation valve 950 requires compression of the pump bulb, resulting in a pressure spike that opens the inflation valve 950. Keeping the valve open is dependent on the pressure differential over the valve seat 955, which is determined by the application of force by the operator as well as spring reload/rate and downstream flow resistance.

Figure 10:
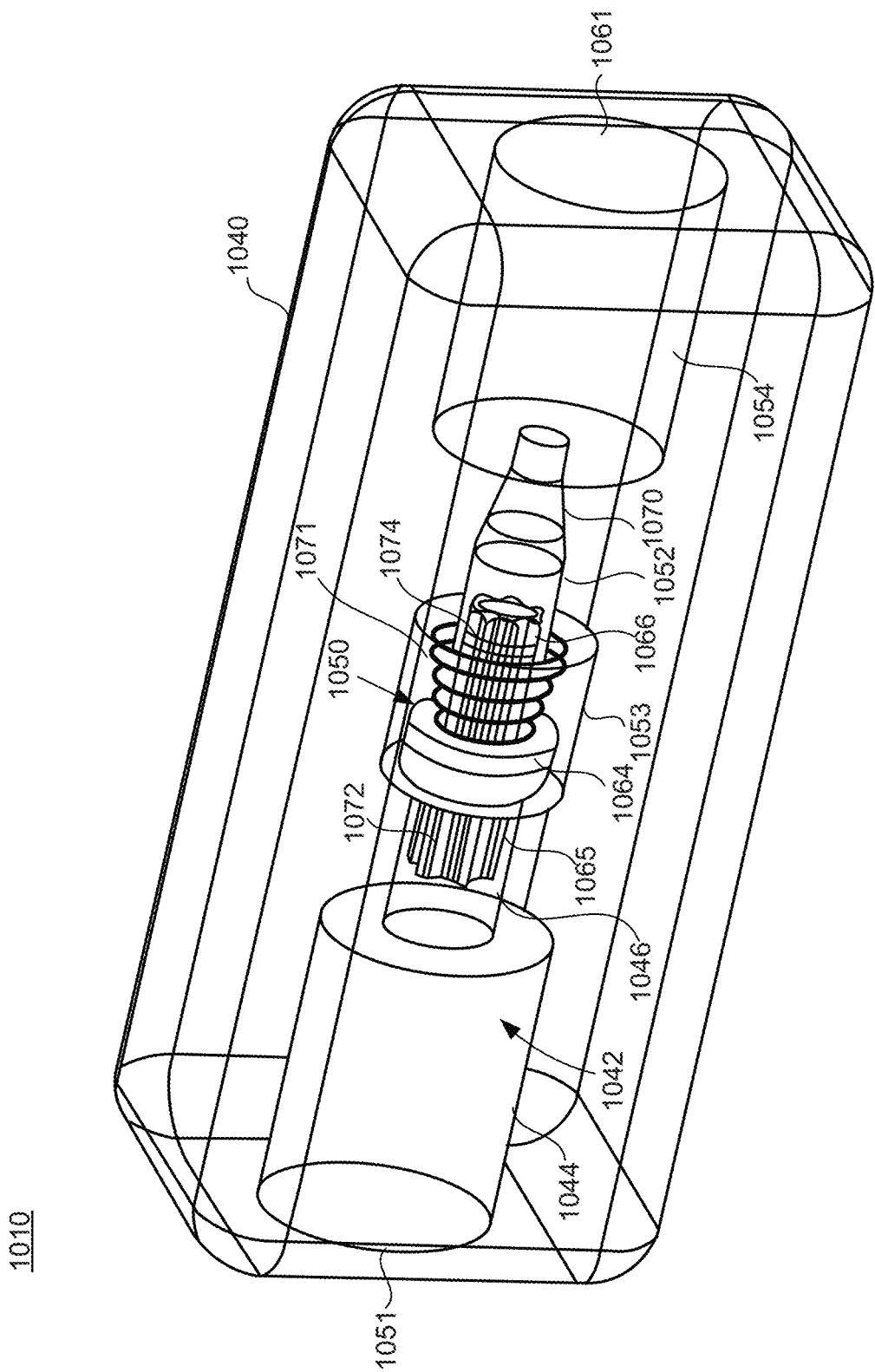
FIG. 10 illustrates an inflation valve assembly according to another aspect.

FIG. 10 illustrates an inflation valve assembly 1010 having a valve body 1040 defining a fluid passageway 1042 and an inflation valve 1050 disposed within the fluid passageway 1042 according to another aspect. The inflation valve assembly 1010 includes a biasing member 1071 configured to bias the inflation valve 1050 to a closed position. In some examples, the inflation valve 1050 is a low resistance inflation valve.

In some examples, the inflation valve 1050 is a spherical fluted valve with guide protrusions on in-flow and out-flow sides. In some examples, the inflation valve 1050 includes a valve member 1064, a first guide member 1065, and a second guide member 1066. The inflation valve 1050 has the same features and operates in the same manner as the inflation valve 950 of FIG. 9 except the valve member 1064 has a different design than the valve member 964 of FIG. 9. As such, the inflation valve 1050 may include one or more of the features described with reference to FIG. 9 (or any combination thereof). In some examples, as shown in FIG. 10, the valve member 1064 is a spherical member. The surface of the valve member 1064 may be smooth (e.g., devoid of surface features such as ridges, grooves, protrusions).

The first guide member 1065 and the second guide member 1066 may extend on opposite ends of the valve member 1064. The first guide member 1065 may include a plurality of grooves 1072. The second guide member 1066 may include a plurality of grooves 1074. Since the first guide member 1065 and the second guide member 1066 are the same as the first guide member 965 and the second guide member 966, respectively, the details are omitted for the sake of brevity.

The valve body 1040 defines a first opening 1051 and a second opening 1061, and the fluid passageway 1042 extends between the first opening 1051 and the second opening 1061. The first opening 1051 is fluidly coupled to the pump bulb (e.g., 106, 206), and the second opening 1061 is fluidly coupled to the inflatable member (e.g., 104, 204). The fluid passageway 1042 is a cavity in the valve body 1040. The fluid passageway 1042 has multiple sizes along a length of the valve body 1040. In some examples, the fluid passageway 1042 is a cylindrical cavity having segments with different diameters. The fluid passageway 1042 may include a first end section 1044 (defining the first opening 1051), a second end section 1054 (defining the second opening 1061), a first flow section 1046, a second flow section 1052, and a central section 1053. The second flow section 1052 may include a tapered portion 1070. The sections of the fluid passageway 1042 may include any of the features described with reference to the previous figures.

Figure 11:
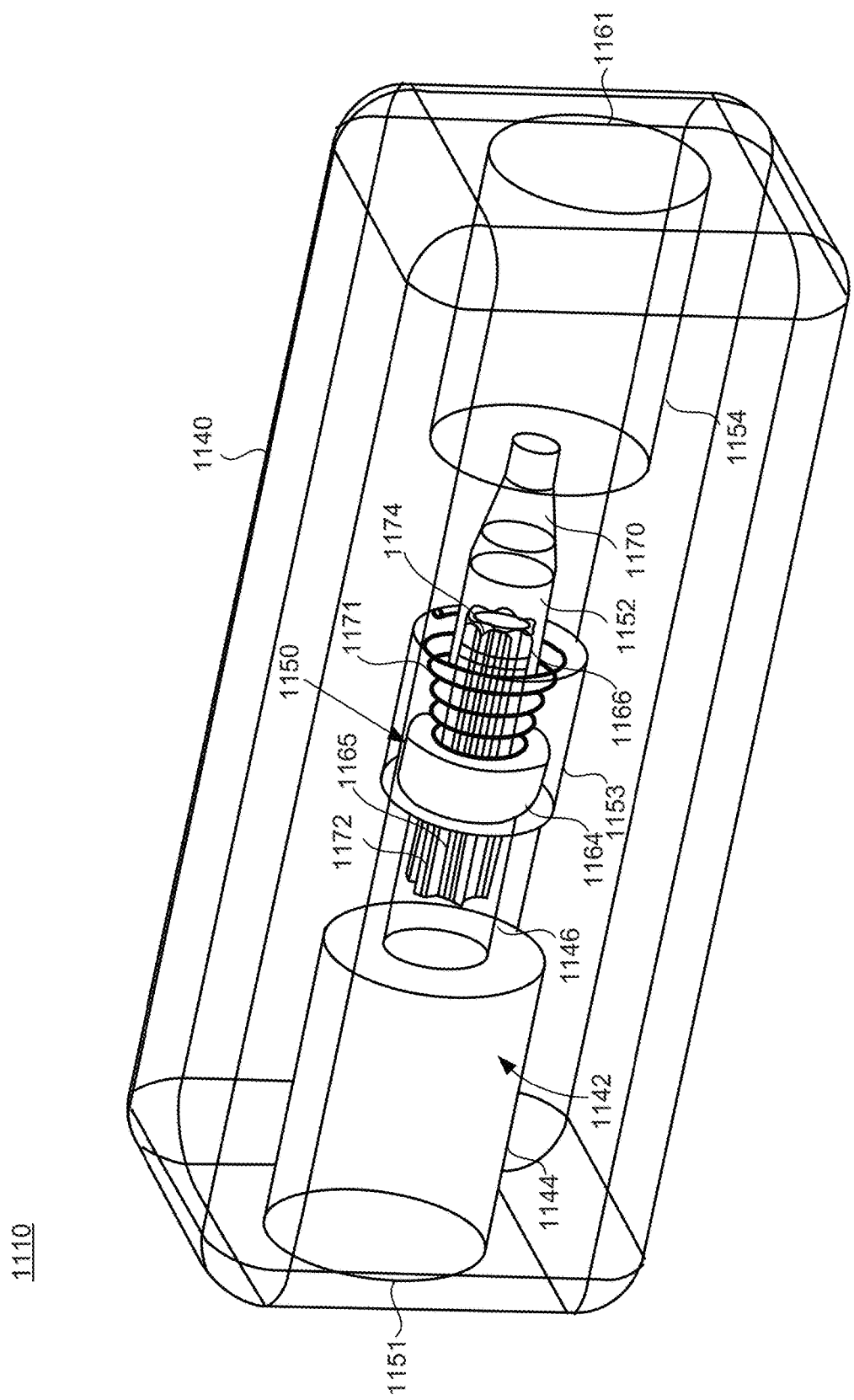
FIG. 11 illustrates an inflation valve assembly according to another aspect.

FIG. 11 illustrates an inflation valve assembly 1110 having a valve body 1140 defining a fluid passageway 1142 and an inflation valve 1150 disposed within the fluid passageway 1142 according to another aspect. In some examples, the inflation valve 1150 is a low resistance inflation valve. The inflation valve assembly 1110 includes a biasing member 1171 configured to bias the inflation valve 1150 to a closed position.

In some examples, the inflation valve 1150 is a cylindrical fluted valve with guide protrusions on in-flow and out-flow sides. In some examples, the inflation valve 1150 includes a valve member 1164, a first guide member 1165, and a second guide member 1166. The inflation valve 1150 has the same features and operates in the same manner as the inflation valve 950 of FIG. 9 except the valve member 1164 has a different design than the valve member 964 of FIG. 9. As such, the inflation valve 1150 may include one or more of the features described with reference to FIG. 9 (or any combination thereof). In some examples, as shown in FIG. 11, the valve member 1164 is a cylindrical member. The surface of the valve member 1164 may be smooth (e.g., devoid of surface features such as ridges, grooves, protrusions).

The first guide member 1165 and the second guide member 1166 may extend on opposite ends of the valve member 1164. The first guide member 1165 may include a plurality of grooves 1172. The second guide member 1166 may include a plurality of grooves 1174. Since the first guide member 1165 and the second guide member 1166 are the same as the first guide member 965 and the second guide member 966, respectively, the details are omitted for the sake of brevity.

The valve body 1140 defines a first opening 1151 and a second opening 1161, and the fluid passageway 1142 extends between the first opening 1151 and the second opening 1161. The first opening 1151 is fluidly coupled to the pump bulb (e.g., 106, 206), and the second opening 1161 is fluidly coupled to the inflatable member (e.g., 104, 204). The fluid passageway 1142 is a cavity in the valve body 1140. The fluid passageway 1142 has multiple sizes along a length of the valve body 1140. In some examples, the fluid passageway 1142 is a cylindrical cavity having segments with different diameters. The fluid passageway 1142 may include a first end section 1144 (defining the first opening 1151), a second end section 1154 (defining the second opening 1161), a first flow section 1146, a second flow section 1152, and a central section 1153. The second flow section 1152 may include a tapered portion 1170. The sections of the fluid passageway 1142 may include any of the features described with reference to the previous figures.

Figure 12:
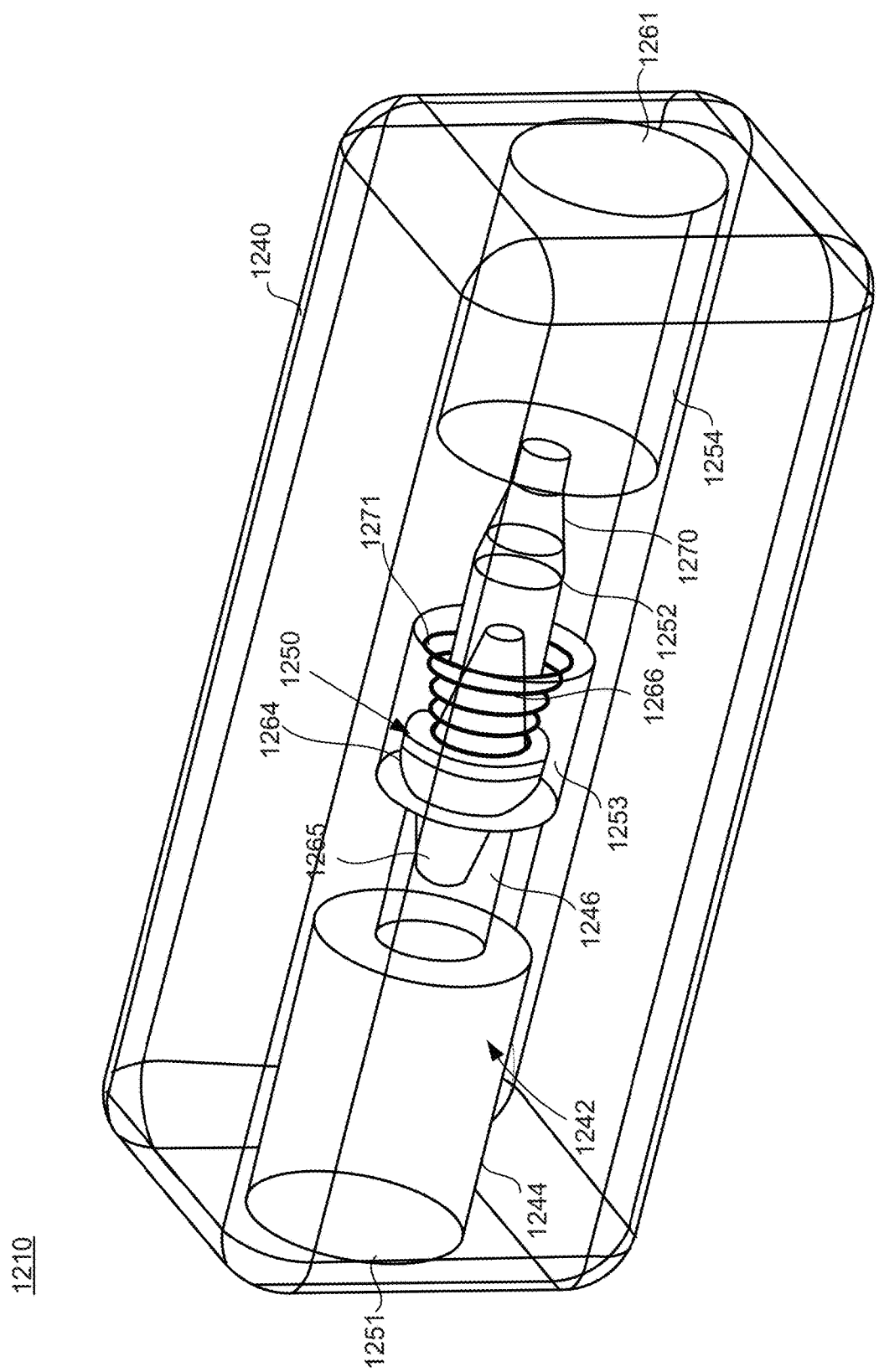
FIG. 12 illustrates an inflation valve assembly according to another aspect.

FIG. 12 illustrates an inflation valve assembly 1210 having a valve body 1240 defining a fluid passageway 1242 and an inflation valve 1250 disposed within the fluid passageway 1242 according to another aspect. In some examples, the inflation valve 1250 is a low resistance inflation valve. The inflation valve assembly 1210 includes a biasing member 1271 configured to bias the inflation valve 1250 to a closed position.

The inflation valve 1250 includes a valve member 1264, a first guide member 1265, and a second guide member 1266. The valve member 1264 may include a three-dimensional object. In some examples, the valve member 1264 includes a curved portion. In some examples, the valve member 1264 includes a round portion. In some examples, the surface of the valve member 1264 is relatively smooth or devoid of surface features (e.g., ridges, grooves, protrusions).

The first guide member 1265 and the second guide member 1266 may extend on opposite sides of the valve member 1264. The first guide member 1265 may include a conical member. In some examples, the surface of the first guide member 1265 is smooth (e.g., devoid of surface features such as ridges, protrusions, grooves). The second guide member 1266 may include a conical member. In some examples, the surface of the second guide member 1266 is smooth (e.g., devoid of surface features such as ridges, protrusions, grooves). In some examples, the length of the second guide member 1266 may be same as the length of the first guide member 1265. In some examples, the length of the second guide member 1266 is different than the length of the first guide member 1265.

The valve body 1240 defines a first opening 1251 and a second opening 1261, and the fluid passageway 1242 extends between the first opening 1251 and the second opening 1261. The first opening 1251 is fluidly coupled to the pump bulb (e.g., 106, 206), and the second opening 1261 is fluidly coupled to the inflatable member (e.g., 104, 204). The fluid passageway 1242 is a cavity in the valve body 1240. The fluid passageway 1242 has multiple sizes along a length of the valve body 1240. In some examples, the fluid passageway 1242 is a cylindrical cavity having segments with different diameters. The fluid passageway 1242 may include a first end section 1244 (defining the first opening 1251), a second end section 1254 (defining the second opening 1261), a first flow section 1246, a second flow section 1252, and a central section 1253. The second flow section 1252 may include a tapered portion 1270. The sections of the fluid passageway 1242 may include any of the features described with reference to the previous figures.

Figure 13:
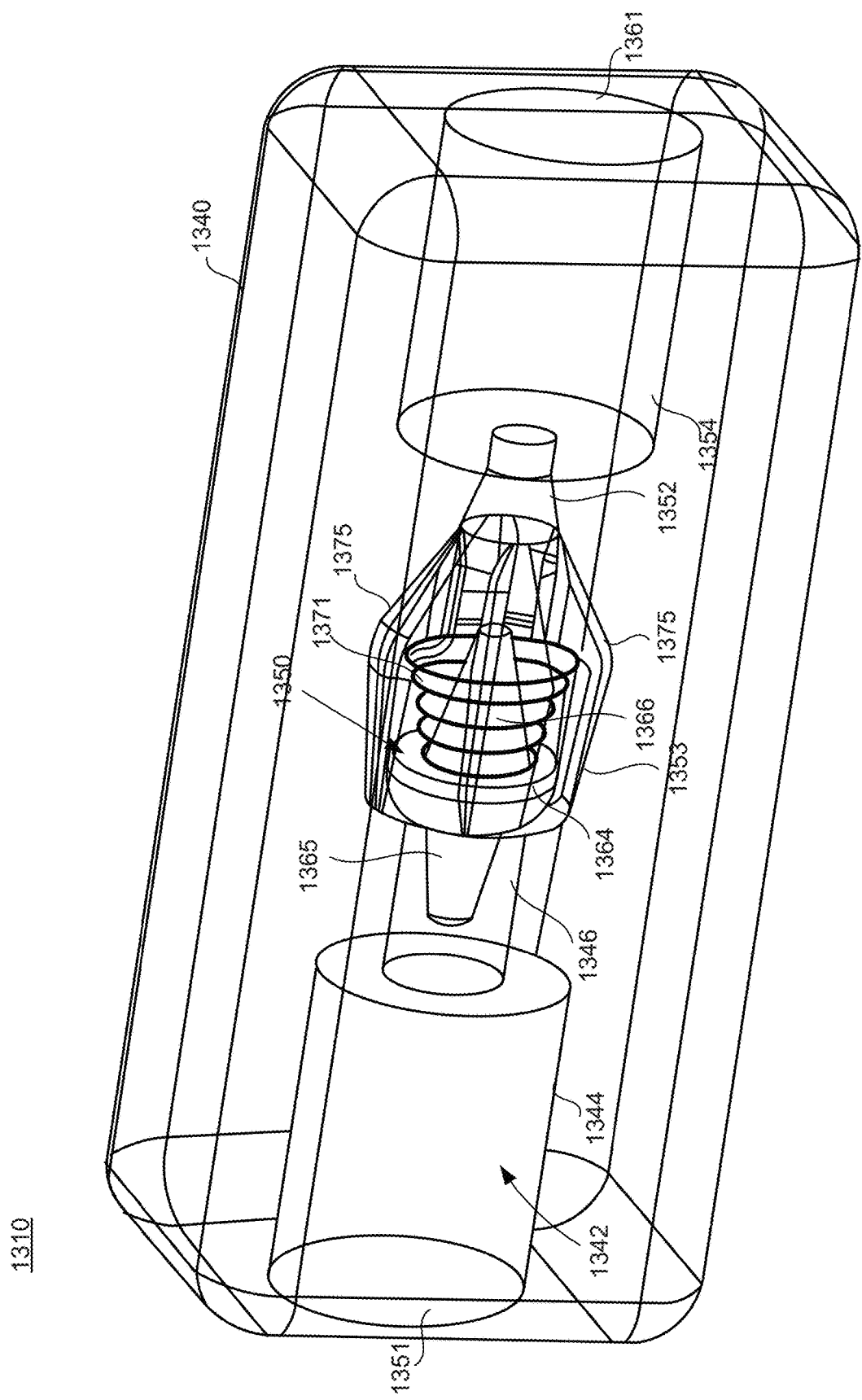
FIG. 13 illustrates an inflation valve assembly according to another aspect.
Figure 14:
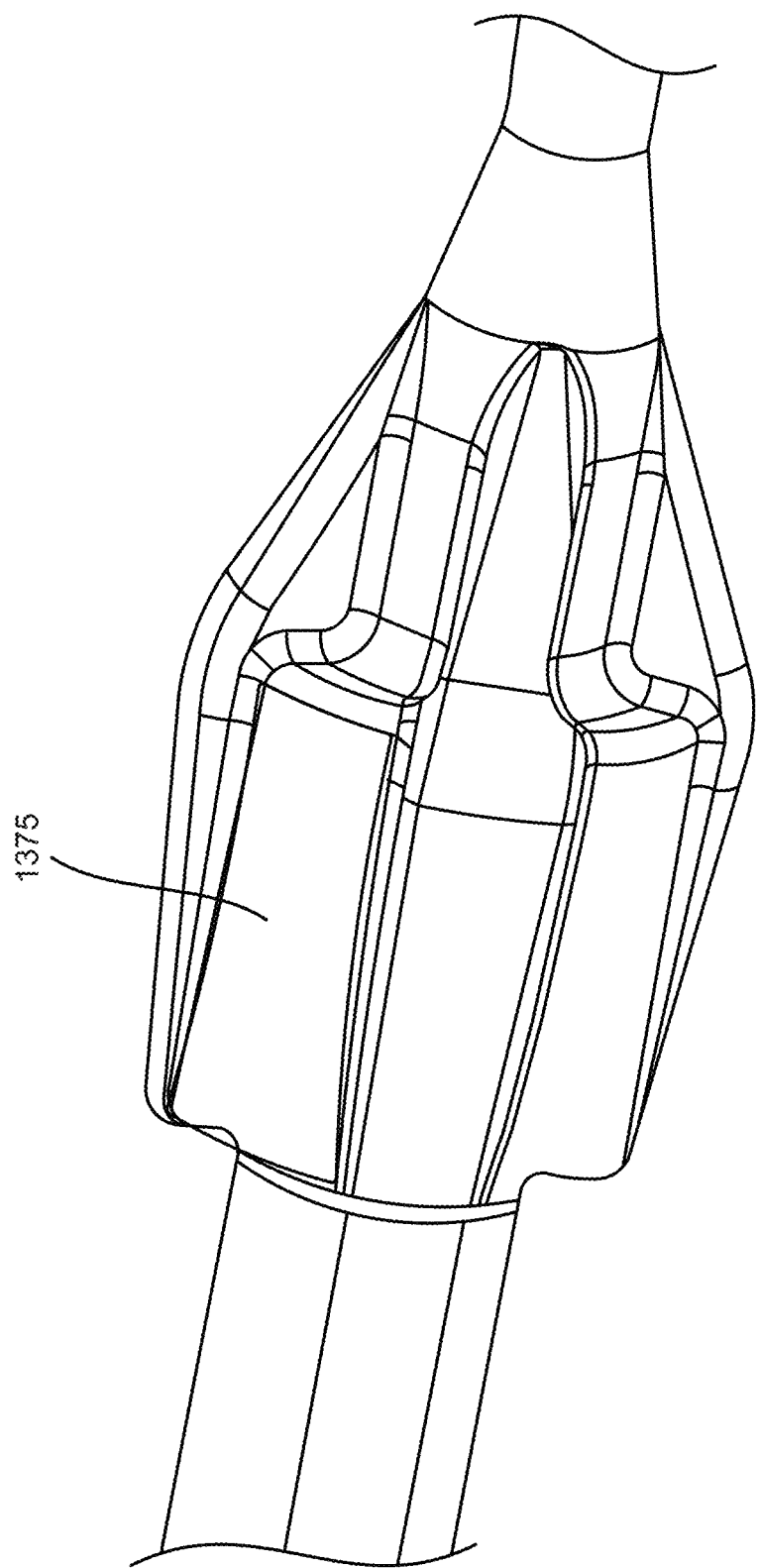
FIG. 14 illustrates a perspective of an overflow channel according to an aspect.
Figure 15:
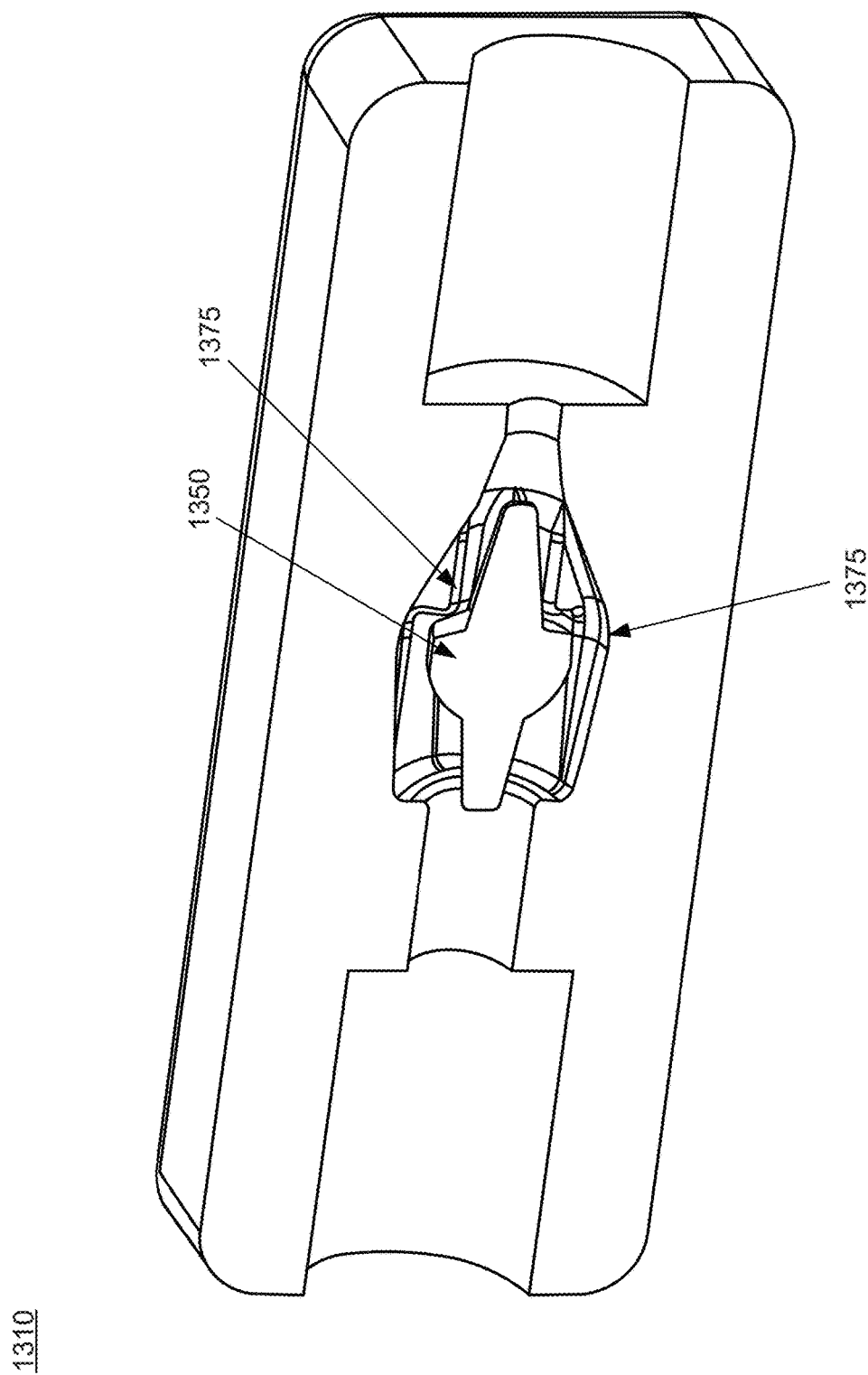
FIG. 15 illustrates a cross-sectional view of an inflation valve in an open position according to an aspect.
Figure 16:
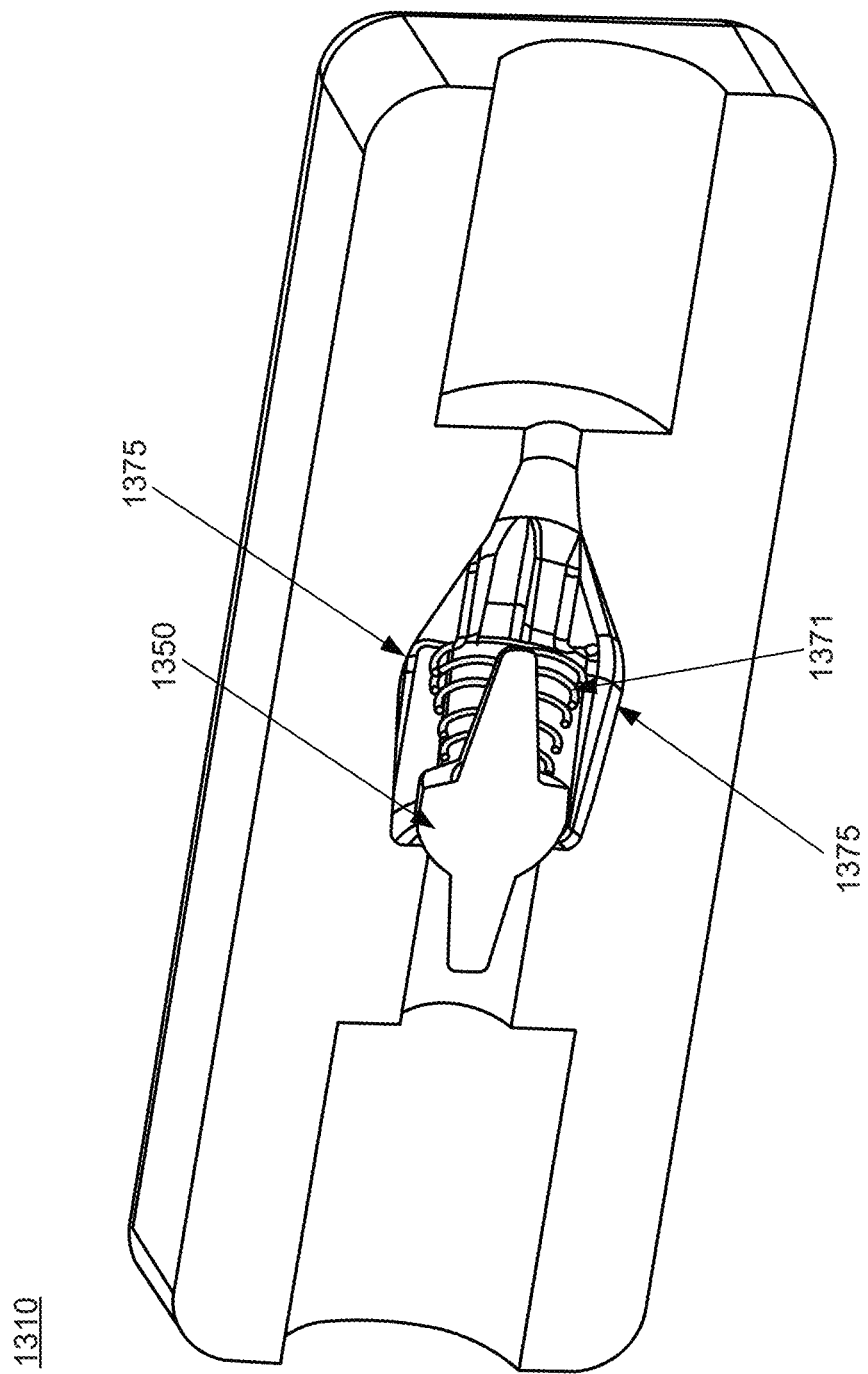
FIG. 16 illustrates a cross-sectional view of the inflation valve in a closed position according to an aspect.

FIG. 13 illustrates an inflation valve assembly 1310 having a valve body 1340 defining a fluid passageway 1342 and an inflation valve 1350 disposed within the fluid passageway 1342 according to another aspect. The inflation valve assembly 1310 is the same as the inflation valve assembly 1210 except a portion of the fluid passageway 1342 and/or the valve body 1340 has a different design that includes the addition of overflow channels 1375. The overflow channels 1375 provide fluid bypass around a compressed (e.g., fully compressed) biasing member 1371 during maximum system flow rates. FIG. 14 illustrates a perspective of the overflow channels 1375 according to an aspect. FIG. 15 illustrates a cross-sectional view of the inflation valve 1350 in an open position according to an aspect. FIG. 16 illustrates a cross-sectional view of the inflation valve 1350 in a closed position according to an aspect.

The inflation valve 1350 includes a valve member 1364, a first guide member 1365, and a second guide member 1366. The valve body 1340 defines a first opening 1351 and a second opening 1361, and the fluid passageway 1342 extends between the first opening 1351 and the second opening 1361. The fluid passageway 1342 may include a first end section 1344 (defining the first opening 1351), a second end section 1354 (defining the second opening 1361), a first flow section 1346, a second flow section 1352, and a central section 1353.

In the open position (as shown in FIG. 15), the pump bulb is being compressed at a force and rate determined by the patient. This force and rate, along with backpressure, will determine the valve position with respect to seat. In the open position, the inflation valve 1350 is fully open for maximum flow (e.g., fully compressed), biasing member 1371 is not shown in FIG. 15), and positioned off the seat allowing fluid to transfer to the inflation member. The overflow channels 1375 are designed such that they do not restrict flow at maximum system flow rates when the biasing member 1371 is fully compressed and in a solid condition. In the closed position (as shown in FIG. 16), the pump bulb has been released by the patient and the biasing member 1371 in conjunction with the cylinder back pressure force the inflation valve 1350 closed. In the closed position, the inflation valve 1350 is fully seated. The overall travel of the inflation valve 1375 has been designed such that the inflation valve 1350 can return to a seated position maintaining a reduced volume of fluid loss as a result of fluid backflow into the pump cavity.

Figure 17:
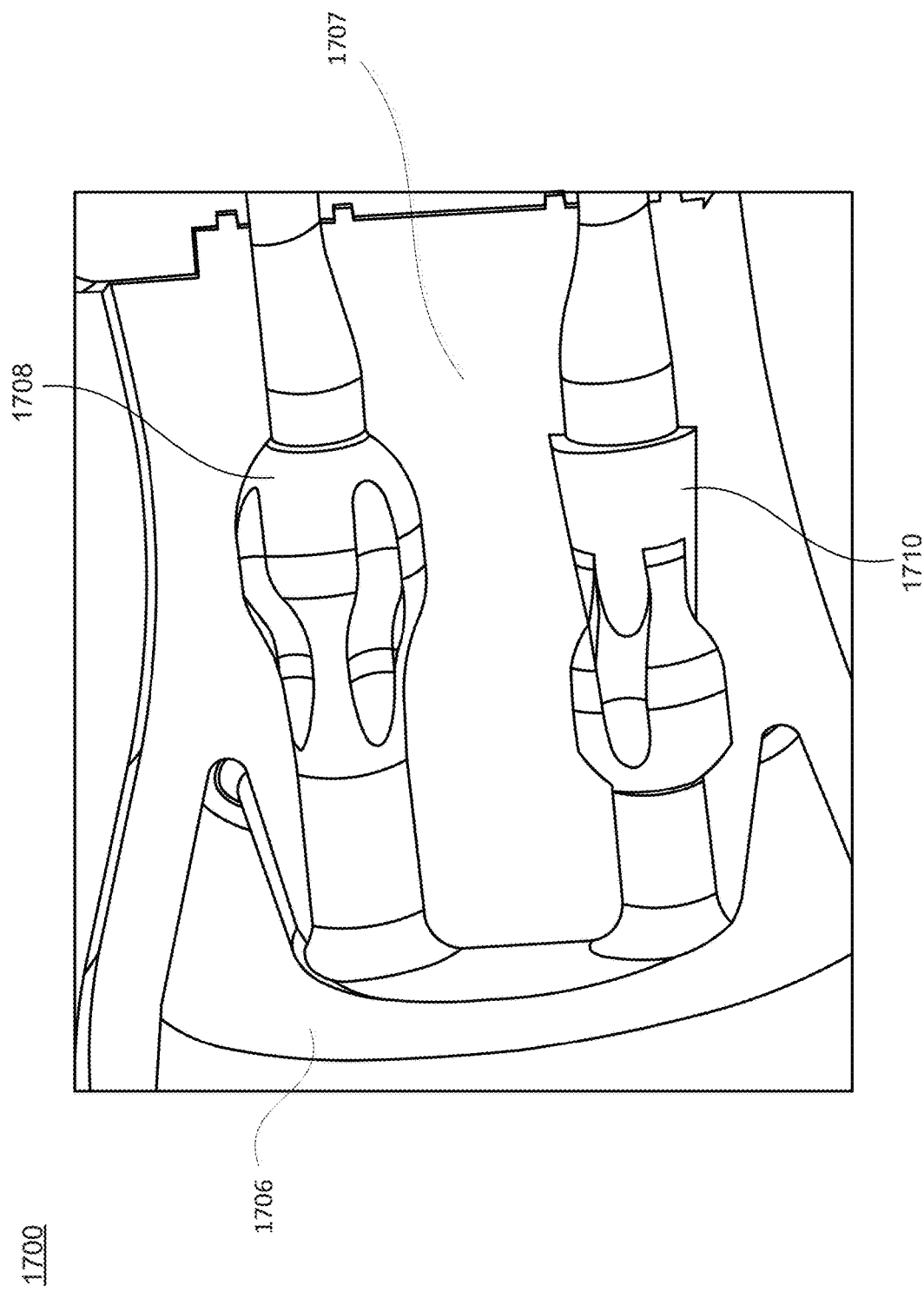
FIG. 17 illustrates a portion of inflatable penile prosthesis having an inflation valve assembly and a refill valve assembly to an aspect.

FIG. 17 illustrates a portion of inflatable penile prosthesis 1700 according to an aspect. FIG. 17 shows a portion of a pump bulb 1706 in fluid communication with a valve body 1707 having a refill valve assembly 1708 and an inflation valve assembly 1710. The refill valve assembly 1708 may be any of the refill valve assemblies discussed herein, and the inflation valve assembly 1710 may be any of the inflation valve assemblies discussed herein.

Figure 18B:
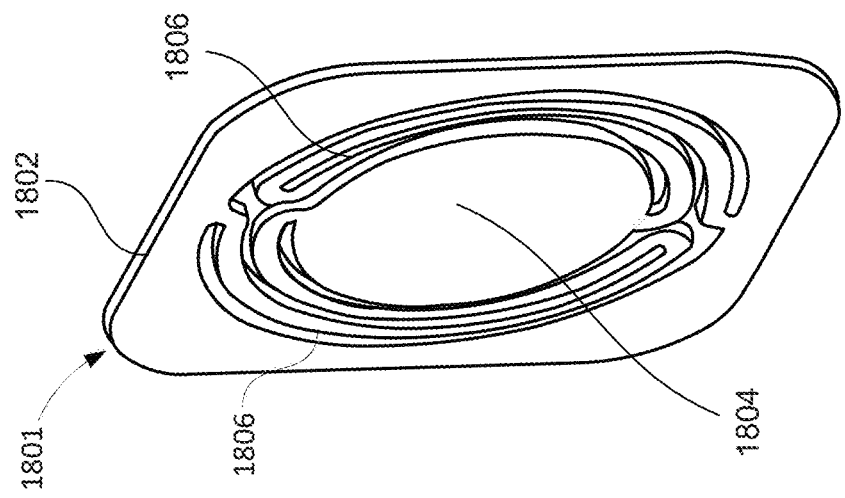
FIG. 18B illustrates a flapper valve in a closed position according to an aspect.
Figure 18A:
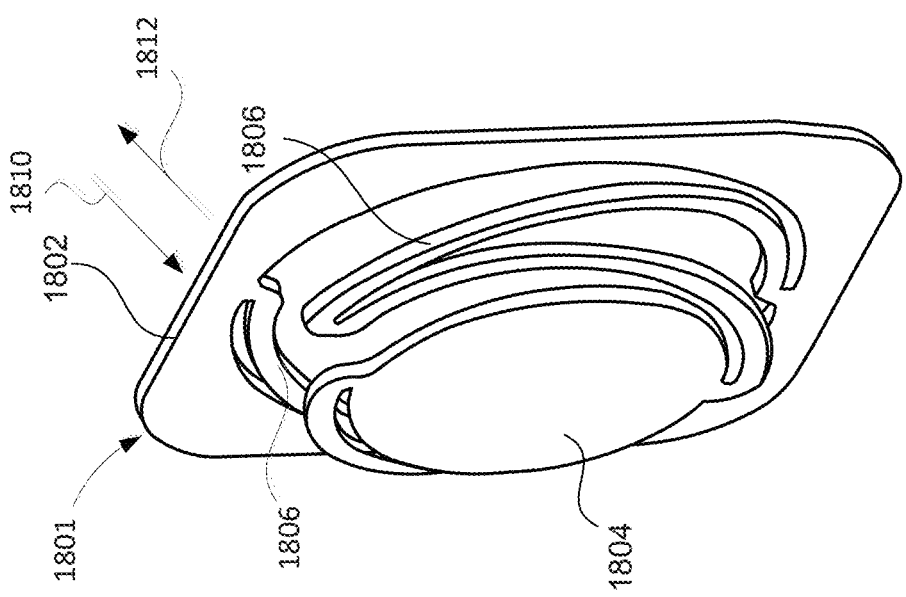
FIG. 18A illustrates a flapper valve in an open position according to an aspect.

FIG. 18A illustrates a flapper valve 1801 in an open position according to an aspect. FIG. 18B illustrates the flapper valve 1801 in a closed position according to an aspect. In some examples, the flapper valve 1801 is an inflation valve. In some examples, the flapper valve 1801 is a refill valve.

The flapper valve 1801 includes an outer structural member 1802, a valve head 1804, and a plurality of spring struts 1806. The valve head 1804 is connected to the outer structural member 1802 via the spring struts 1806. In some examples, the valve head 1804 is circular. The spring struts 1806 are formed by cutting a check valve pattern into the flapper valve 1801. The valve head 1804 is biased to the closed position in which the valve head 1804, the spring struts 1806, and the outer structural member 1802 are disposed in substantially the same plane. When the flapper valve 1801 is disposed in a fluid passageway and fluid pressure is applied to the valve head 1804, the valve head 1804 moves in a first direction 1810, where the valve head 1804 moves away from the outer structural member 1802. When fluid pressure is removed, the valve head 1804 moves in a second direction 1812. The second direction 1812 is opposite to the first direction 1810. For instance, when fluid pressure is removed, the spring back force of the spring struts 1806 force the valve head 1804 to move back to its original position as shown in FIG. 18B.

The near two-dimensional profile of the valve head 1804 permits the valve head 1804 to be moved out of the flow path more completely (as compared to conventional designs), allowing for higher flow rates at the same pressure drop across the flapper valve 1801. The crack pressure and flow rate of the flapper valve 1801 can be tuned by modifying the spring strut thickness and width to achieve relatively low crack pressures and high flow rates while providing sufficient protection against backflow at pressures exceeding a certain level (e.g., 30 psi). Since the valve seal is incorporated into the valve assembly, the insertion of the valve into the pump body is simplified as the precision alignment of the seal and the valve head 1804 is accomplished during valve assembly and not during insertion of the flapper valve 1801 into the pump housing. This allows for larger tolerances and more process variation in the pump molding without negatively impacting the performance and reliability of the valve assembly.

Due to the low crack pressures, high flow rates, and relatively good resistance to backflow, the flapper valve 1801 may be used in refill and/or inflation valve applications. When the patient compresses the pump, the pressure increases within the bulb cavity and eventually opens the flapper valve 1801, allowing fluid to pass over the flapper valve 1801. The initial opening of the valve requires pressure to be applied over the valve (e.g., crack pressure) either by the patient/physician squeezing the pump bulb (in the case of being used as an inflation valve) or by the vacuum pressure created by the pump bulb expanding after it has been squeezed (in the case of being used as a refill valve). Keeping the valve open is dependent on the pressure differential over the inflation valve seat, which is determined by the continued application of pressure as mentioned above in addition to the spring preload/rate of the spring struts and downstream flow resistance.

Figure 19:
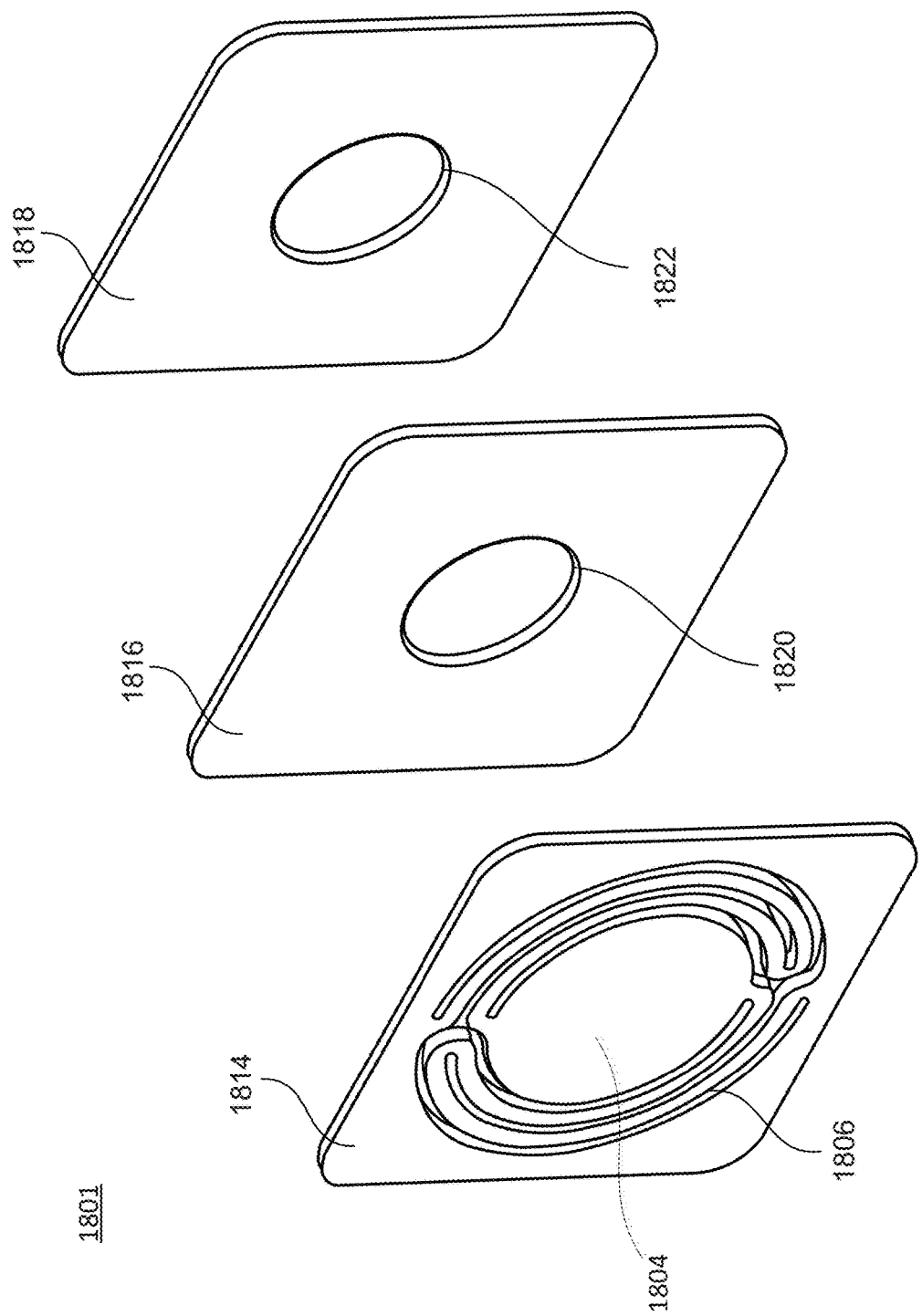
FIG. 19 illustrates the flapper valve according to another aspect.

FIG. 19 illustrates the flapper valve 1801 according to another aspect. The flapper valve 1801 includes a valve head layer 1814, elastomeric seal layer 1816, and a backplate layer 1818. In some examples, the valve head layer 1814 includes a nitinol or other suitable material. In some examples, the back plate layer 1818 includes a nitinol or other suitable material. The back plate layer 1818 may be relatively rigid. In some examples, the back plate layer 1818 is more rigid than the elastomeric seal layer 1816. The valve head layer 1814 includes the spring struts 1806. The elastomeric seal layer 1816 defines a through hole 1820. The backplate layer 1818 defines a through hole 1822. The diameter of the valve head 1804 may be larger than the diameter of the through hole 1820. The diameter of the valve head 1804 may be larger than the diameter of the through hole 1822. Backflow may be prevented due to the larger size of the valve head 1804 as compared as to the through hole 1820 and the through hole 1822.

The superelastic properties of the nitinol or other suitable material provide the spring force to return the flapper valve 1801 to the closed position when pressure is not being applied to the flapper valve 1801. The diameter of the throughhole 1820 and the diameter of the throughhole 1822 are sized to a smaller diameter than the valve head 1804 to prevent reverse-flow.

Figure 20:
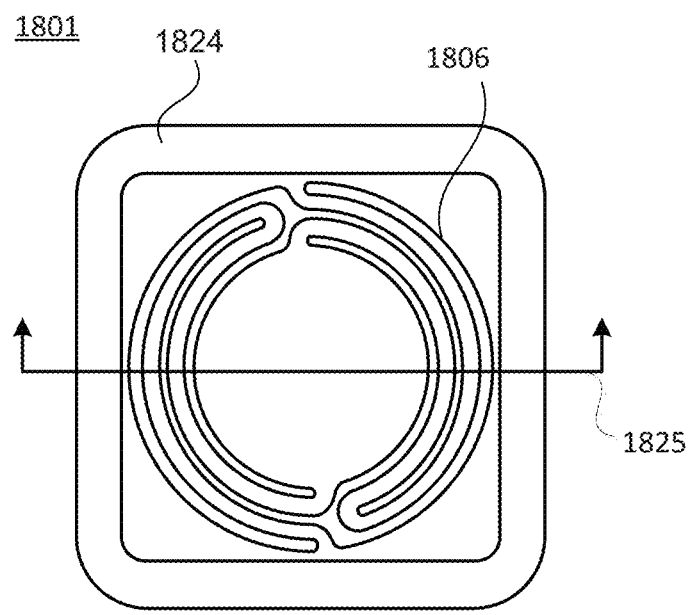
FIG. 20 illustrates a top view of the flapper valve according to an aspect.
Figure 21:
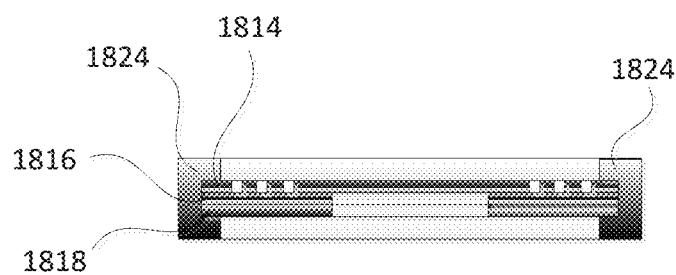
FIG. 21 illustrates a cross-sectional view of the flapper valve according to an aspect.

FIG. 20 illustrates a front view of the flapper valve 1801 according to an aspect. FIG. 21 illustrates a cross-sectional view of the flapper valve 1801, taken along line 1825, according to an aspect. The flapper valve 1801 includes outer overmold 1824. The outer overmold 1824 may surround the outer perimeter of the valve head layer 1814, the elastomeric seal layer 1816, and the backplate layer 1818.

Figure 22:
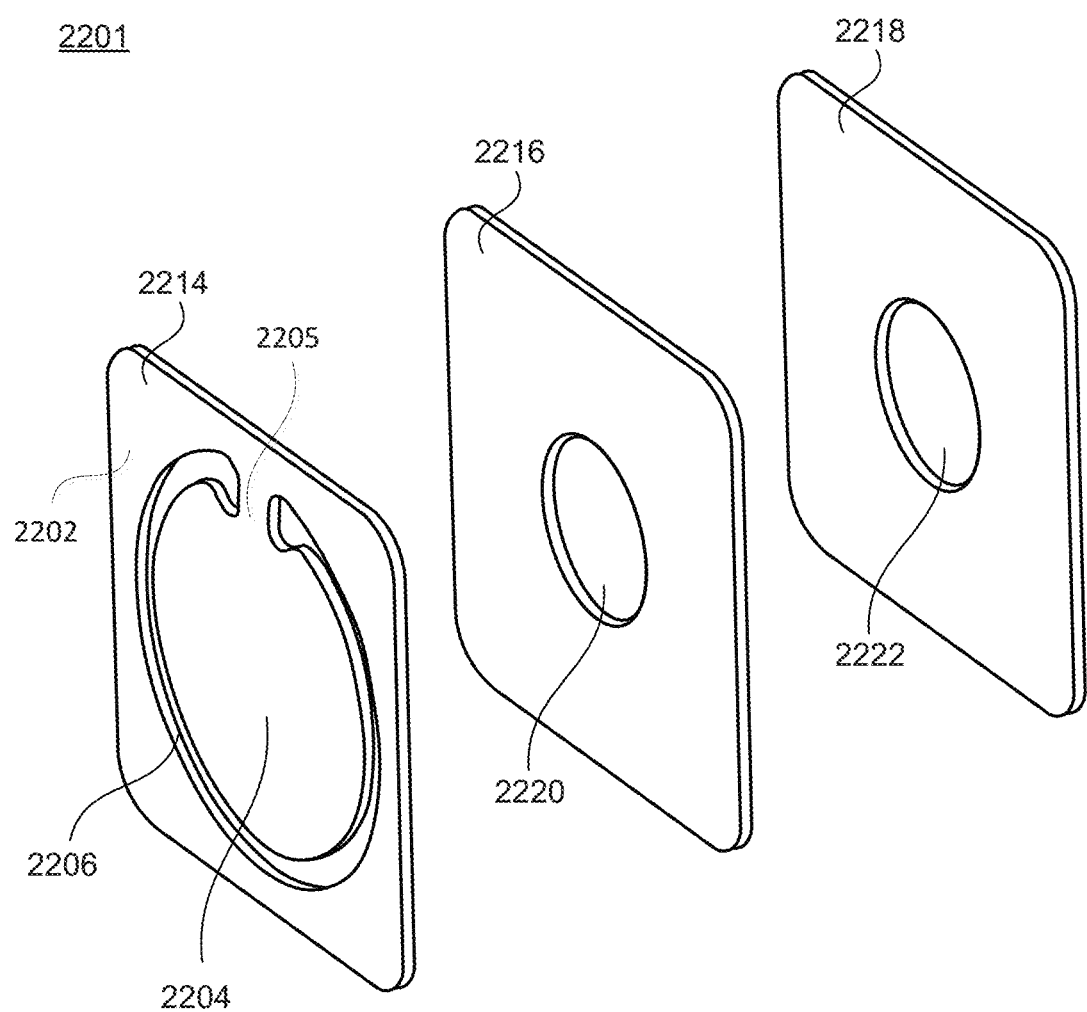
FIG. 22 illustrates a flapper valve according to another aspect.

FIG. 22 illustrates a flapper valve 2201 according to another aspect. The flapper valve 2201 includes a valve head layer 2214, elastomeric seal layer 2216, and a backplate layer 2218. In some examples, the valve head layer 2214 includes a nitinol or other suitable material. In some examples, the back plate layer 2218 includes a nitinol or other suitable material. The backplate layer 2218 may be relatively rigid. In some examples, the backplate layer 2218 is more rigid than the elastomeric seal layer 2216. The valve head layer 2214 includes a slot 2206 having an un-closed loop. The shape of the slot 2206 defines the shape of the valve head 2204. The valve head 2204 is connected to an outer structural member 2202 via portion 2205. The elastomeric seal layer 2216 defines a through hole 2220. The backplate layer 2218 defines a through hole 2222. The diameter of the valve head 2204 may be larger than the diameter of the through hole 2220. The diameter of the valve head 2204 may be larger than the diameter of the through hole 2222.

Figure 23:
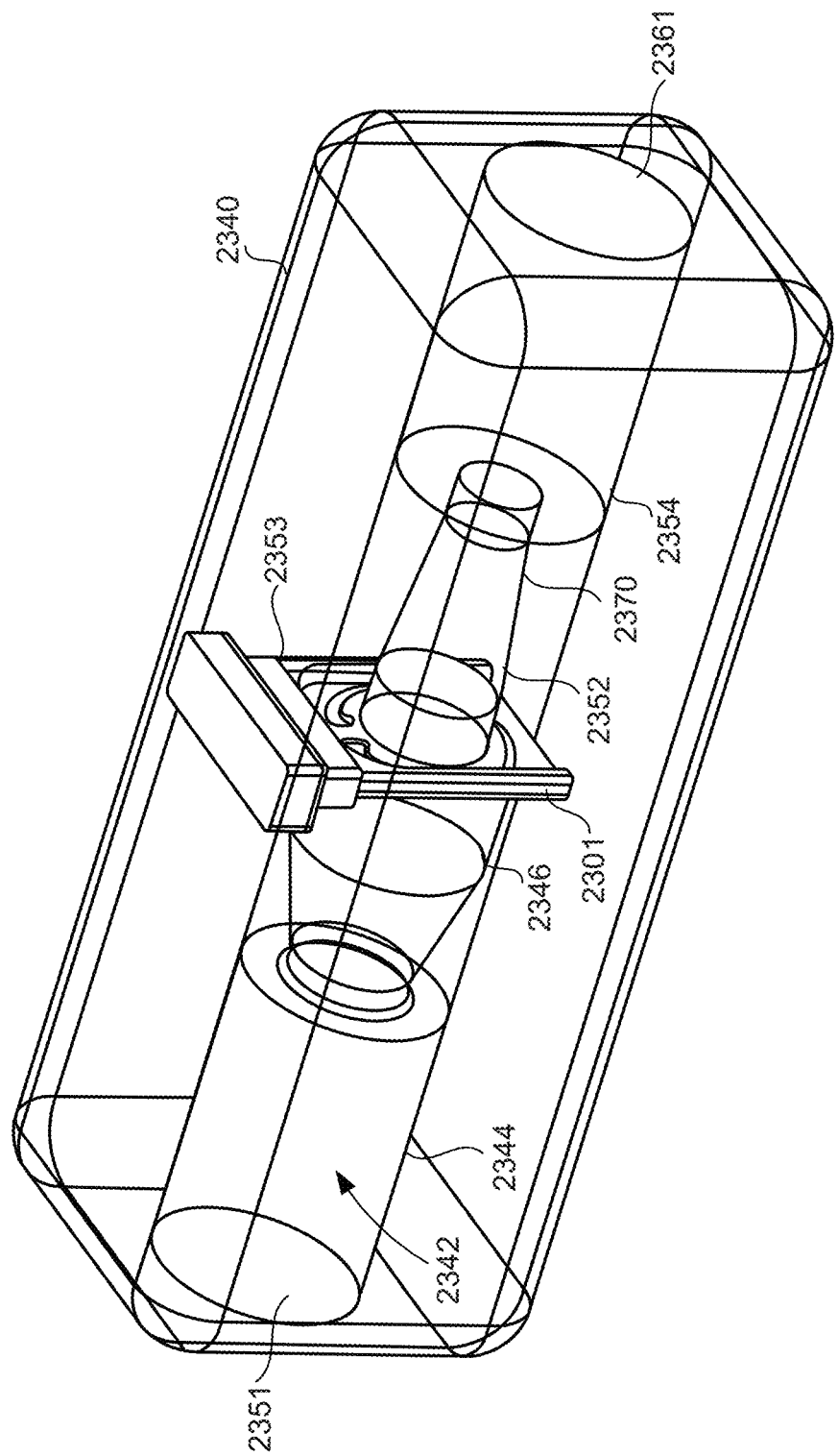
FIG. 23 illustrates a flapper valve assembly according to an aspect.

FIG. 23 illustrates a valve body 2340 having a flapper valve 2301 according to an aspect. The valve body 2340 defines a fluid passageway 2342. The flapper valve 2301 is disposed within the fluid passageway 2342. The valve body 2340 defines a first opening 2351 and a second opening 2361, and the fluid passageway 2342 extends between the first opening 2351 and the second opening 2361.

The fluid passageway 2342 is a cavity in the valve body 2340. The fluid passageway 2342 has multiple sizes along a length of the valve body 2340. In some examples, the fluid passageway 2342 is a cylindrical cavity having segments with different diameters. The fluid passageway 2342 may include a first end section 2344, and a second end section 2354. The fluid passageway 2342 includes a first flow section 2346, a second flow section 2352, and a slot 2353 disposed between the first flow section 2346 and the second flow section 2352. The second flow section 2352 includes a tapered portion 2370 that tapers to a smaller diameter towards the second end section 2354. The flapper valve 2301 is configured to be inserted into the fluid passageway 2342 via the slot 2353.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
a reservoir configured to hold fluid;
an inflatable member; and
a pump assembly configured to facilitate a transfer of a fluid from the reservoir to the inflatable member,
the pump assembly including a pump bulb, and a valve body defining a fluid passageway, the valve body including a refill valve disposed in the fluid passageway, the refill valve including a valve member, a first protrusion, and a second protrusion, the first protrusion being spaced from the second protrusion,
in response to the pump bulb being compressed, the valve member is configured to move within the fluid passageway in a first direction to a closed position in which the valve member blocks the fluid from being transferred around the refill valve,
in response to the pump bulb being uncompressed, the valve member is configured to move within the fluid passageway in a second direction to an open position in which the valve member is configured to contact the first protrusion and the second protrusion and allow the fluid to transfer around the refill valve.

2. The inflatable penile prosthesis of claim 1, wherein the valve member includes a valve seat portion configured to block the fluid passageway in response to the valve member being in the closed position.

3. The inflatable penile prosthesis of claim 1, wherein the valve member includes a tapered seat portion configured to block the fluid passageway in response to the valve member being in the closed position.

4. The inflatable penile prosthesis of claim 1, wherein the valve member defines a plurality of grooves.

5. The inflatable penile prosthesis of claim 1, wherein the refill valve includes a first guide member that extends from a first side of the valve member in the first direction, and a second guide member that extends from a second side of the valve member in the second direction.

6. The inflatable penile prosthesis of claim 5, wherein at least one of the first guide member or the second guide member includes a plurality of grooves.

7. The inflatable penile prosthesis of claim 1, wherein the refill valve is devoid of a biasing member that biases the valve member to either the closed position or the open position.

8. The inflatable penile prosthesis of claim 1, wherein the fluid passageway is a first fluid passageway, the valve body including a second fluid passageway and an inflation valve disposed within the second fluid passageway, the inflation valve including a valve member disposed within the second fluid passageway and configured to move between an open position and a closed position, the inflation valve including a biasing member configured to bias the valve member of the inflation valve to the closed position.

9. The inflatable penile prosthesis of claim 8, wherein the valve member of the inflation valve includes a valve seat portion configured to block the second fluid passageway in response to the valve member of the inflation valve being in the closed position.

10. The inflation penile prosthesis of claim 8, wherein the inflation valve includes a first guide member that extends from the valve member of the inflation valve in the first direction, and a second guide member that extends from the valve member of the inflation valve in the second direction.

11. A valve assembly for an inflatable penile prosthesis, the valve assembly comprising:
a valve body having a first fluid passageway for transfer of fluid between a reservoir and a pump bulb and a second fluid passageway for transfer of fluid between the pump bulb and an inflatable member;
a refill valve disposed in the first fluid passageway, the refill valve having a valve member, wherein in response to the pump bulb being compressed, the valve member is configured to move within the first fluid passageway in a first direction to a closed position in which the valve member blocks the fluid from being transferred around the refill valve, wherein, in response to the pump bulb being uncompressed, the valve member is configured to move within the first fluid passageway in a second direction to an open position in which the valve member is configured to contact a first protrusion and a second protrusion and allows the fluid to transfer around the refill valve; and
an inflation valve disposed in the second fluid passageway.

12. The valve assembly of claim 11, wherein the inflation valve includes a valve member and a biasing member disposed within the second fluid passageway, the biasing member configured to bias the valve member of the inflation valve to a closed position.

13. The valve assembly of claim 12, wherein the second fluid passageway includes:
a first flow section having a first size;
a second flow section having a second size; and
a central section disposed between the first flow section and the second flow section, the central section having a third size, the valve member of the inflation valve and the biasing member being disposed within the central section,
wherein the third size is larger than the second size.

14. The valve assembly of claim 11, wherein the inflation valve includes a flapper valve.

15. The valve assembly of claim 11, wherein the flapper valve includes an outer structural member, a cut pattern, and a valve head, the valve head being configured to move away from the outer structural member in response to fluid force.

16. The valve assembly of claim 11, wherein the first fluid passageway includes:
a first cylindrical section having a first diameter;
a second cylindrical section having a second diameter; and
a central cylindrical section disposed between the first cylindrical section and the second cylindrical section, the central cylindrical section having a third diameter, the valve member of the refill valve being disposed within the central cylindrical section,
wherein the third diameter is larger than the second diameter.

17. An inflatable penile prosthesis comprising:
a reservoir configured to hold fluid;
an inflatable member; and
a pump assembly configured to facilitate a transfer of a fluid from the reservoir to the inflatable member,
the pump assembly including a pump bulb, and a valve body defining a first fluid passageway and a second fluid passageway, the valve body including a refill valve disposed in the first fluid passageway, and an inflation valve disposed in the second fluid passageway,
a refill valve disposed in the first fluid passageway, the refill valve having a valve member, wherein in response to the pump bulb being compressed, the valve member is configured to move within the first fluid passageway in a first direction to a closed position in which the valve member blocks the fluid from being transferred around the refill valve, wherein, in response to the pump bulb being uncompressed, the valve member is configured to move within the first fluid passageway in a second direction to an open position in which the valve member is configured to contact a first protrusion and a second protrusion and allows the fluid to transfer around the refill valve.

18. The inflatable penile prosthesis of claim 17, wherein the refill valve includes a first guide member that extends from a first side of the valve member in the first direction, and a second guide member that extends from a second side of the valve member in the second direction.

19. The inflatable penile prosthesis of claim 1, wherein the refill valve is devoid of a biasing member.

\* \* \* \* \*